(12) United States Patent
Fukai et al.

(10) Patent No.: US 9,188,537 B2
(45) Date of Patent: Nov. 17, 2015

(54) SENSING METHOD AND SENSING DEVICE

(75) Inventors: Toshio Fukai, Ashigarakami-gun (JP); Atsushi Matsumoto, Ashigarakami-gun (JP); Kazuya Matsumoto, Kamiina-gun (KR); Takuro Suyama, Ina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 112 days.

(21) Appl. No.: 14/007,403

(22) PCT Filed: Mar. 5, 2012

(86) PCT No.: PCT/JP2012/055587
§ 371 (c)(1),
(2), (4) Date: Sep. 25, 2013

(87) PCT Pub. No.: WO2012/132775
PCT Pub. Date: Oct. 4, 2012

(65) Prior Publication Data
US 2014/0017799 A1    Jan. 16, 2014

(30) Foreign Application Priority Data

Mar. 29, 2011 (JP) .................................. 2011-072867

(51) Int. Cl.
*G01N 21/64*   (2006.01)
*G01N 33/66*   (2006.01)

(52) U.S. Cl.
CPC .......... *G01N 21/643* (2013.01); *G01N 21/6428* (2013.01); *G01N 33/66* (2013.01); *Y10T 436/144444* (2015.01)

(58) Field of Classification Search
CPC ....... G01N 33/48; G01N 33/49; G01N 33/66; G01N 21/64; G01N 21/6428; G01N 21/643; Y10T 436/144444

USPC .......... 436/63, 95, 164, 172, 147; 422/82.05, 422/82.08, 82.12; 435/14; 600/316, 317, 600/365
See application file for complete search history.

(56) References Cited

U.S. PATENT DOCUMENTS 5,342,789 A    8/1994 Chick et al.
6,330,464 B1   12/2001 Colvin, Jr. et al.
(Continued)

FOREIGN PATENT DOCUMENTS

JP    8-159974 A    6/1996
JP    2883824 B2    4/1999
(Continued)

OTHER PUBLICATIONS

International Search Report (PCT/ISA/210) mailed on May 1, 2012, by the Japanese Patent Office as the International Searching Authority for International Application No. PCT/JP2012/055587.
(Continued)

*Primary Examiner* — Maureen Wallenhorst
(74) *Attorney, Agent, or Firm* — Buchanan Ingersoll & Rooney PC

(57) ABSTRACT

This invention relates to a sensing method and a sensing device for quantifying the concentration of an analyte by using the property that interaction between an analyte and a labeled compound changes fluorescence intensity. A fluorescence sensor is used to acquire fluorescence intensity at predetermined quantification time points. Then, the concentration of an analyte is quantified in accordance with a non-steady concentration quantification law including the relationship between the acquired fluorescence intensity and the time derivative quantity thereof.

18 Claims, 24 Drawing Sheets

(56) References Cited

U.S. PATENT DOCUMENTS 8,649,836 B2 * 2/2014 Shimizu et al. ............... 600/316
2002/0164813 A1 11/2002 Colvin, Jr. et al.

FOREIGN PATENT DOCUMENTS

| JP | 3296556 B2 | 7/2002 |
| JP | 2004-529352 A | 9/2004 |
| JP | 2006-084456 A | 3/2006 |
| WO | WO 2010/119916 A1 | 10/2010 |

OTHER PUBLICATIONS

Written Opinion (PCT/ISA/237) mailed on May 1, 2012, by the Japanese Patent Office as the International Searching Authority for International Application No. PCT/JP2012/055587.

* cited by examiner

SENSING METHOD AND SENSING DEVICE

TECHNICAL FIELD

The present invention relates to a sensing method and a sensing device for quantifying the concentration of analytes based on the intensity of fluorescence, which changes due to an interaction between the analytes and a labeled compound.

BACKGROUND ART

Recently, there has been developed a sensing device for quantifying the concentration of analytes based on the intensity of fluorescence, which changes due to an interaction between the analytes and a labeled compound. One proposed application is a device for continuously quantifying the concentration of glucose with a sensor embedded in the body of an examinee (see U.S. Pat. No. 6,330,464). By using the device to acquire and analyze time-series data of the blood sugar levels of a diabetic patient, it is possible to appropriately establish a drug administration protocol for stabilizing the blood sugar level, and to offer guidance to the patient on how to improve his or her lifestyle habits.

A fluorescence signal that corresponds to a glucose concentration is obtained from a fluorochrome compound, which combines with glucose, for example, to emit fluorescence (see Japanese Patent No. 2883824). As disclosed in Japanese Patent No. 3296556, it has also been proposed to use, as a fluorescence signal, a change in the extent of a fluorescence resonance energy transfer, which occurs when a compound of fluorescein-labeled dextran and rhodamine-labeled concanavalin A, which does not cause a fluorescence signal change simply by combining with glucose, is dissociated by glucose, and to correlate the fluorescence signal with glucose concentration.

In the absence of an analyte concentration change, i.e., in a state of equilibrium, an analyte concentration [A(t)] and a fluorescence intensity F(t) are related to each other according to the following equation (1):

$$-(\alpha_1[A(t)]+\alpha_2)F(t)+\alpha_3[A(t)]=0 \quad (1)$$

where $\alpha_1$ through $\alpha_3$ represent quantification coefficients attributed to a reaction rate constant, etc. In particular, $\alpha_2$ corresponds to a reaction rate constant in relation to dissociation between the labeled compound and a third compound. Equation (1) may be simplified in order to calculate [A(t)] according to the following equation (2):

$$[A(t)] = \frac{\alpha_2 F(t)}{\alpha_3 - \alpha_1 F(t)} \quad (2)$$

According to such a system, the analyte concentration [A(t)] may be quantified continuously by acquiring the fluorescence intensity F(t) at a predetermined quantification time t, and quantifying the acquired fluorescence intensity F(t) according to equation (2).

SUMMARY OF INVENTION

According to the results of a study conducted by the inventor of the present invention, it has been found that when a time-dependent change in the fluorescence intensity F(t) is steep with respect to a response rate for emitting fluorescence, the quantified value of the analyte concentration [A(t)] becomes delayed in time, thereby lowering the accuracy of the quantification according to equation (2). Therefore, when blood sugar levels are quantified and measured, for example, the accuracy of quantification in a low body temperature state and a low blood sugar state, which is required especially for the analysis of time-series data of blood sugar levels, tends to be lowered.

The present invention has been made in an effort to solve the aforementioned problems. It is an object of the present invention to provide a sensing method and a sensing device, which are capable of quantifying a concentration of analytes highly accurately, even if a time-dependent change in fluorescence intensity is steep.

According to the present invention, there is provided a sensing method of quantifying a concentration of analytes based on the intensity of fluorescence, which changes due to an interaction between the analytes and a labeled compound, comprising an acquisition step of acquiring the intensity of fluorescence at a predetermined quantification time using a fluorescence sensor, and a quantification step of quantifying the concentration of the analytes according to a non-steady concentration quantification rule representative of a relationship between the acquired intensity of fluorescence and a time derivative of the intensity of fluorescence.

Since the concentration of the analytes is quantified according to a non-steady concentration quantification rule representative of a relationship between the acquired intensity of fluorescence and a time derivative thereof, it is possible to quantify the concentration of the analytes in view of not only a present intensity of fluorescence but also a time-dependent change in the intensity of fluorescence. Therefore, even if the time-dependent change in the intensity of fluorescence is relatively steep compared with the response rate at which fluorescence is emitted, the concentration of the analytes can be quantified highly accurately.

The non-steady concentration quantification rule preferably is determined based on a chemical reaction formula representative of a bond dissociation reaction between the analytes and the labeled compound.

The sensing method preferably further comprise a selection step of selecting a concentration quantification rule from a steady concentration quantification rule in relation to the intensity of fluorescence and at least one non-steady concentration quantification rule, depending on a time-dependent change in the acquired intensity of fluorescence and/or an ambient temperature. In addition, the quantification step preferably quantifies the concentration of the analytes according to the selected concentration quantification rule. Since a concentration quantification formula suitable for the tendency of the time-dependent change in the intensity of fluorescence can be selected, the concentration of the analytes can be quantified highly accurately regardless of the measuring environment.

The selection step preferably selects the steady concentration quantification rule if the ambient temperature exceeds a first threshold value, and selects the non-steady concentration quantification rule if the ambient temperature does not exceed the first threshold value. Therefore, even if the time-dependent change in the intensity of fluorescence is steep, the time-dependent change is immediately reflected in the quantified value of the concentration, resulting in highly accurate quantified results.

The selection step preferably selects the steady concentration quantification rule if the time-dependent change in the intensity of fluorescence does not exceed a second threshold value, and selects the non-steady concentration quantification rule if the time-dependent change in the intensity of fluorescence exceeds the second threshold value. Therefore, even if the time-dependent change in the intensity of fluorescence is steep, the time-dependent change is immediately reflected in the quantified value of the concentration, resulting in highly accurate quantified results.

The selection step preferably further selects the concentration quantification rule from a plurality of non-steady concentration quantification rules having different degrees of contribution of the time derivative. By changing the degree of contribution in a stepwise manner, it is possible to reduce discontinuity between quantified values owing to differently selected concentration quantification rules, thereby avoiding the risk of localized reductions in quantification accuracy.

The selection step preferably increases the degrees of contribution as the ambient temperature decreases. In this manner, it is possible to obtain more accurate quantified results in agreement with an actual system.

The selection step preferably increases the degrees of contribution as the time-dependent change in the intensity of fluorescence increases. In this manner, it is possible to obtain more accurate quantified results in agreement with an actual system.

The sensing method preferably further comprises a changing step of changing a sampling interval for the intensity of fluorescence depending on the time-dependent change in the intensity of fluorescence and/or the ambient temperature. Accordingly, the changing step is capable of both maintaining quantification accuracy and lowering electric power consumption, by appropriately changing the sampling interval at which the intensity of fluorescence is sampled.

The sensing method preferably further comprises a correction step of correcting the quantified concentration of the analytes depending on the degree of permeation of the analytes into the fluorescence sensor. Accordingly, a reduction in quantification accuracy caused by a time delay in permeation of the analytes can be prevented from occurring.

According to the present invention, there also is provided a sensing device for quantifying the concentration of analytes based on an intensity of fluorescence, which changes due to an interaction between the analytes and a labeled compound, comprising a fluorescence sensor for acquiring the intensity of fluorescence at a predetermined quantification time, and a concentration quantifier for quantifying the concentration of the analytes according to a non-steady concentration quantification rule representative of a relationship between the intensity of fluorescence acquired by the fluorescence sensor and a time derivative of the intensity of fluorescence.

The non-steady concentration quantification rule preferably is determined based on a chemical reaction formula representative of a bond dissociation reaction between the analytes and the labeled compound.

The sensing device preferably further comprises a quantification rule selector for selecting a concentration quantification rule from a steady concentration quantification rule in relation to the intensity of fluorescence and at least one non-steady concentration quantification rule, depending on a time-dependent change in the acquired intensity of fluorescence and/or an ambient temperature. The concentration quantifier preferably quantifies the concentration of the analytes according to the concentration quantification rule selected by the quantification rule selector.

The quantification rule selector preferably selects the steady concentration quantification rule if the ambient temperature exceeds a first threshold value, and selects the non-steady concentration quantification rule if the ambient temperature does not exceed the first threshold value.

The quantification rule selector preferably selects the steady concentration quantification rule if the time-dependent change in the intensity of fluorescence does not exceed a second threshold value, and selects the non-steady concentration quantification rule if the time-dependent change in the intensity of fluorescence exceeds the second threshold value.

The quantification rule selector preferably further selects the concentration quantification rule from a plurality of non-steady concentration quantification rules having different degrees of contribution of the time derivative.

The quantification rule selector preferably increases the degrees of contribution as the ambient temperature decreases.

The quantification rule selector preferably increases the degrees of contribution as the time-dependent change in the intensity of fluorescence increases.

The sensing device preferably further comprises a sampling interval changer for changing a sampling interval for the intensity of fluorescence depending on the time-dependent change in the intensity of fluorescence and/or the ambient temperature.

The concentration quantifier preferably corrects the quantified concentration of the analytes depending on a degree of permeation of the analytes into the fluorescence sensor.

With the sensing method and the sensing device according to the present invention, since the concentration of analytes is quantified according to the non-steady concentration quantification rule representative of a relationship between the acquired intensity of fluorescence and a time derivative thereof, it is possible to quantify the concentration of the analytes in view of not only a present intensity of fluorescence, but also a time-dependent change in the intensity of fluorescence. Therefore, even if the time-dependent change in the intensity of fluorescence is relatively steep compared with the response rate at which fluorescence is emitted, the concentration of the analytes can be quantified highly accurately.

DESCRIPTION OF EMBODIMENTS

Sensing methods according to preferred embodiments of the present invention in connection with sensing devices for carrying out the sensing methods will be described in detail below with reference to the accompanying drawings.

First, the configuration of a sensing device 10, which is common to first through third embodiments of the present invention, will be described below with reference to FIGS. 1 through 3.

Figure 1:
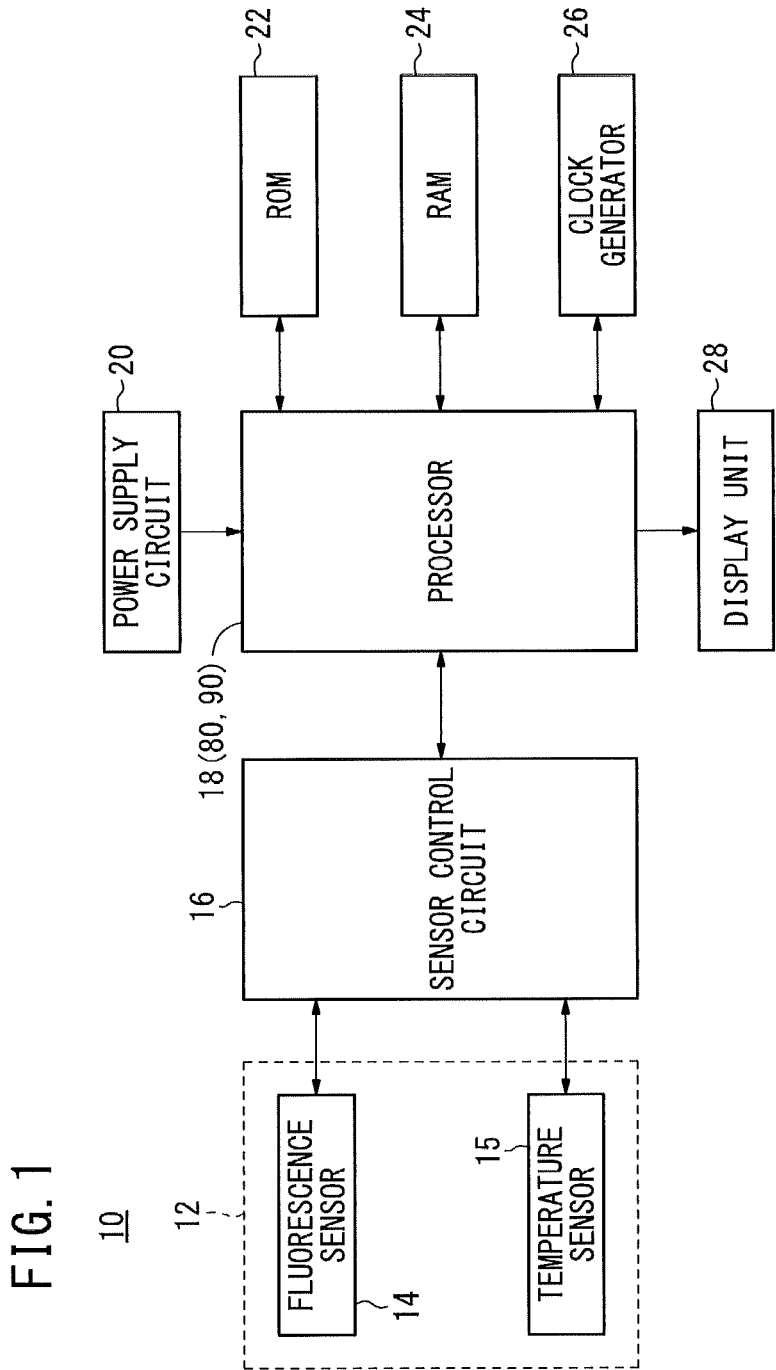
FIG. 1 is a block diagram of a sensing device according to first through third embodiments of the present invention.

As shown in FIG. 1, the sensing device 10 has a sensor assembly 12, which includes a fluorescence sensor 14 and a temperature sensor 15, a sensor control circuit 16, a processor 18 (80, 90), a power supply circuit 20, a ROM 22, a RAM 24, a clock generator 26, and a display unit 28.

The fluorescence sensor 14 acquires a signal (hereinafter referred to as a "fluorescence signal"), which is dependent on the intensity of fluorescence F emitted due to an interaction between analytes A and a labeled compound. The fluorescence F may be light emitted due to a bond or dissociation between the analytes A and the labeled compound, or light may be emitted due to a bond or dissociation between a third compound that differs from the analytes A and the labeled compound. The concentration of the analytes A can be quantified based on the fluorescence signal, regardless of the type of light that is emitted as the fluorescence F. The temperature sensor 15 acquires a signal (hereinafter referred to as a "temperature signal"), which is dependent on the ambient temperature θ in the vicinity of the fluorescence sensor 14.

The sensor control circuit 16 energizes the fluorescence sensor 14 and the temperature sensor 15, and controls the fluorescence sensor 14 and the temperature sensor 15 to acquire a fluorescence signal and a temperature signal, respectively. The processor 18, which comprises a CPU, an MPU, or the like, reads programs recorded in the ROM 22 and performs various signal processing routines to be described later. The power supply circuit 20 supplies electric power to various components in the sensing device 10 including the processor 18. The RAM 24 is capable of reading and writing a fluorescence signal input from the fluorescence sensor 14, a temperature signal input from the temperature sensor 15, and various other data required to carry out the sensing methods according to the present invention. The clock generator 26 generates a clock signal having a predetermined cyclic period and supplies the generated clock signal to the processor 18, which makes it possible to control the timings at which fluorescence signals and temperature signals are acquired. The display unit 28 visualizes and displays various items of information in relation to the concentration of analytes A quantified by the processor 18. The display unit 28 is a monochromatic or color display module, which may comprise a liquid crystal panel, an organic EL (Electro-Luminescence) panel, an inorganic EL panel, or the like.

Structural details of the sensor assembly 12 will be described below with reference to FIGS. 2 and 3.

Figure 2:
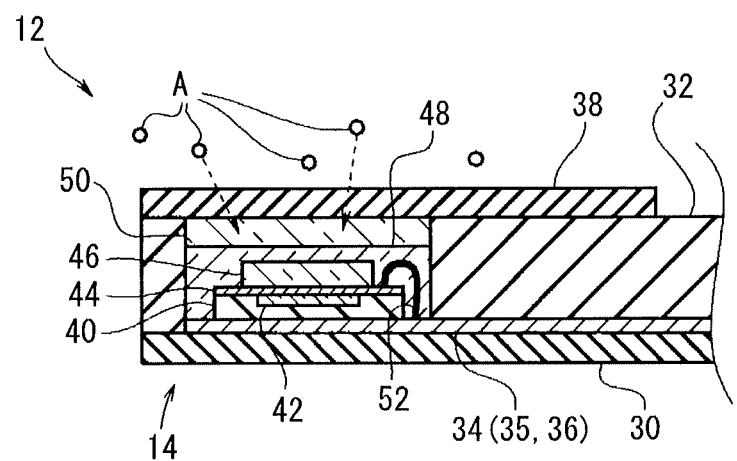
FIG. 2 is a cross-sectional view of a sensor assembly shown in FIG. 1.

As shown in FIG. 2, the sensor assembly 12 has a substantially rectangular housing 30. The housing 30 is of a hollow structure and houses therein the fluorescence sensor 14, a base 32, and six metal wires 34, 35, 36. The housing 30 and the base 32 are made of a resin such as polyimide, parylene (poly-para-xylylene), or cyclic polyolefine. The material of the housing 30 and the base 32 may contain a light blocking material such as carbon black for blocking external light. The housing 30 has a surface (entry surface) 38, which is made of hydrogel and carbon black or the like, which allows analytes A to pass therethrough while blocking external light.

The fluorescence sensor 14 includes a base layer 40 made of silicon or the like, a photodiode device (hereinafter referred to as a "PD device") 42, a first protective film (not shown), a filter 44, a light-emitting diode device (hereinafter referred to as an "LED device") 46, a second protective film 48 made of epoxy resin or the like, and an indicator layer 50.

The PD device 42 is disposed on the surface of the base layer 40. The PD device 42 is a photoelectric transducer for converting fluorescence F into electric signals. The PD device 42 may be replaced with any of various other types of photoelectric transducers, including a photoconductor, a phototransistor (PT), etc. The PD device 42 and the metal wires 34 are electrically connected to each other by bonding wires 52, or through interconnections or the like.

The filter 44 comprises an absorptive optical filter for blocking a wavelength range of excited light E emitted by the LED device 46, and for passing fluorescence F, a wavelength of which is longer than the wavelength range of the excited light E.

The LED device 46 is a light-emitting device for emitting excited light E. The LED device 46 may be replaced with any of various light-emitting devices, including an organic EL panel, an inorganic EL panel, a laser diode device, etc. Preferably, the LED device 46 comprises a light-emitting device, which exhibits a high transmittance for fluorescence F, in order to increase the detected amount of fluorescence F, i.e., the amount of fluorescence F received by the PD device 42.

The indicator layer 50 emits fluorescence F depending on the concentration of analytes A, e.g., glucose, which have entered from the entry surface 38. The indicator layer 50 is made of a base material containing a fluorochrome as a labeled compound. If the indicator layer 50 emits fluorescence F due to a dissociation between the labeled compound (e.g., fluorescein-labeled dextran) and a third compound (e.g., rhodamine-labeled concanavalin A), then the base material of the indicator layer 50 may contain a third component as well as the labeled compound. Alternatively, the indicator layer 50 may include a mechanism for adding the third component.

Figure 3:
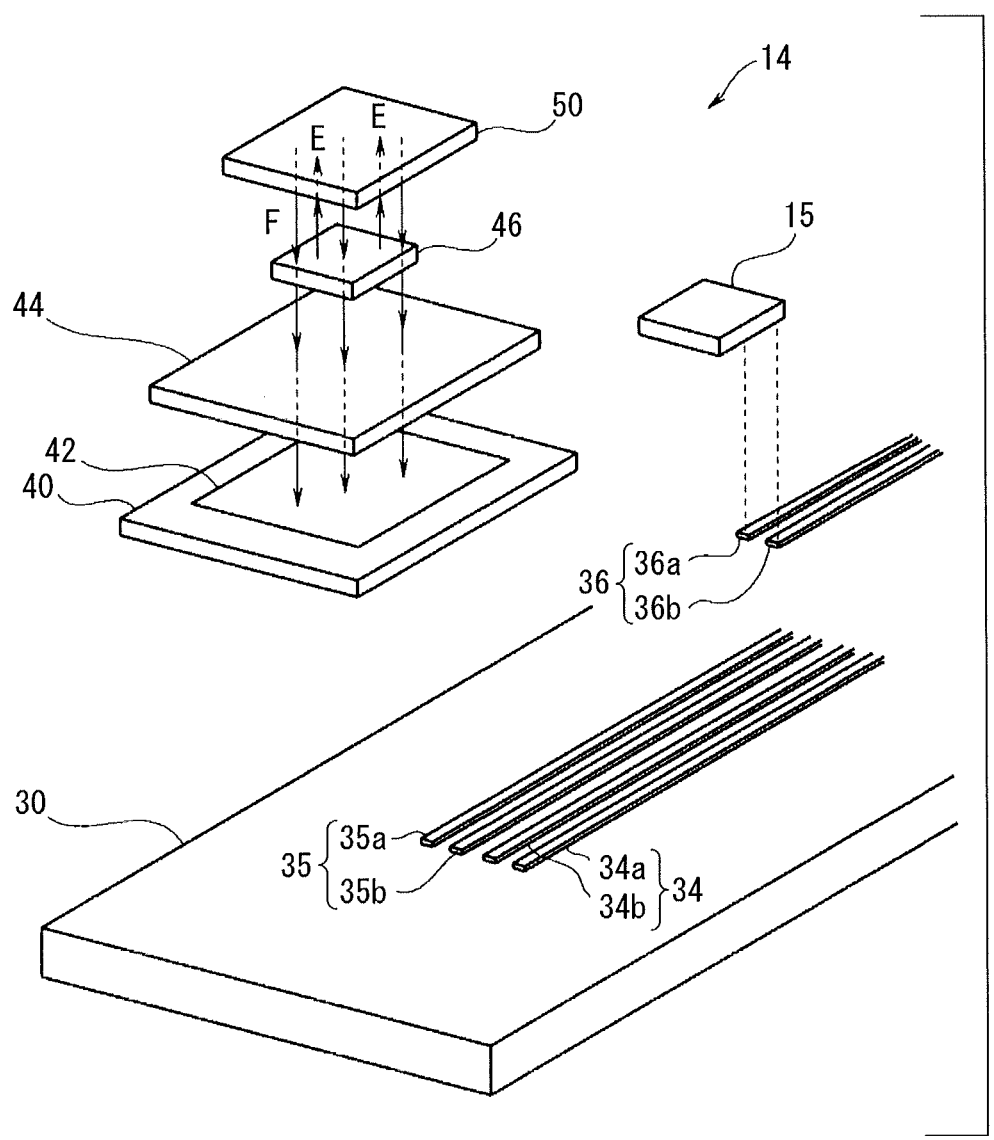
FIG. 3 is an exploded perspective view of the sensor assembly shown in FIG. 1.

As shown in FIG. 3, the housing 30 houses therein the temperature sensor 15 (see FIG. 1) for acquiring a temperature signal in the vicinity of the fluorescence sensor 14. The temperature sensor 15 may comprise an optical temperature sensor such as a fluorescence thermometer, a thermistor temperature sensor, a thin metal film resistance temperature sensor, or a semiconductor temperature sensor having temperature characteristics based on a forward current across a PN junction. If the temperature sensor 15 comprises a semiconductor temperature sensor, the temperature sensor 15 may be disposed on the base layer 40, similar to the case of the PD device 42.

The metal wires 34, 35, 36, which are made of an electric conductor such as aluminum, copper, or the like, function to increase the rigidity of the housing 30, in addition to functioning as electric wires in the housing 30. The sensor assembly 12 is electrically connected to the sensor control circuit 16 (see FIG. 1) through the metal wires 34, 35, 36. As shown in FIG. 3, the metal wires 34 comprise two metal wires 34a, 34b, the metal wires 35 comprise two metal wires 35a, 35b, and the metal wires 36 comprise two metal wires 36a, 36b. The metal wires 34 (or the metal wires 35) and the metal wires 36 may be electrically insulated from each other by an insulating layer, not shown, disposed therebetween.

The sensor control circuit 16 can acquire a fluorescence signal from the PD device 42 through the metal wires 34. The sensor control circuit 16 can supply energizing electric power to the LED device 46 through the metal wires 35. The sensor control circuit 16 can acquire a temperature signal from the temperature sensor 15 through the metal wires 36.

Operations of the sensor assembly 12 will be described below. If the sensor assembly 12 is in the form of a needle, then the sensor assembly 12 can continuously measure the concentration of analytes A in the body of an examinee by puncturing the examinee with a tip of the needle and holding the tip of the needle in the examinee. With the tip of the sensor assembly 12 held in the examinee, certain analytes A enter into the housing 30 from the entry surface 38 and remain in and around the indicator layer 50.

The sensor control circuit 16 supplies energizing electric power through the metal wires 35 of the fluorescence sensor 14 to the LED device 46, so as to enable the LED device 46 to emit excited light E. Excited light E emitted from the LED device 46 is applied to the indicator layer 50. The indicator layer 50 emits fluorescence F, an intensity of which is commensurate with the concentration of the analytes A, due to an interaction between the analytes A and the labeled compound, or due to an interaction between a third compound and the labeled compound.

Fluorescence F emitted from the indicator layer 50 passes through the LED device 46 and the filter 44 to the PD device 42, which photoelectrically converts the fluorescence F into a fluorescence signal. The fluorescence signal is transmitted through the metal wires 34 to the sensor control circuit 16. A temperature signal from the temperature sensor 15 is transmitted through the metal wires 36 to the sensor control circuit 16.

In this manner, the fluorescence sensor 14 acquires a fluorescence signal and the temperature sensor 15 acquires a temperature signal. The sensor assembly 12 shown in FIGS. 2 and 3 is applicable to various applications, such as an oxygen sensor, a glucose sensor, a pH sensor, an immunity sensor, a microorganism sensor, or the like. The sensor assembly 12 is not limited to the illustrated structure, but may include various other structures.

First Embodiment

A sensing method according to the first embodiment will be described below with reference to FIGS. 4 through 10. In the present description, results obtained by quantifying glucose as analytes A will primarily be described.

Figure 4:
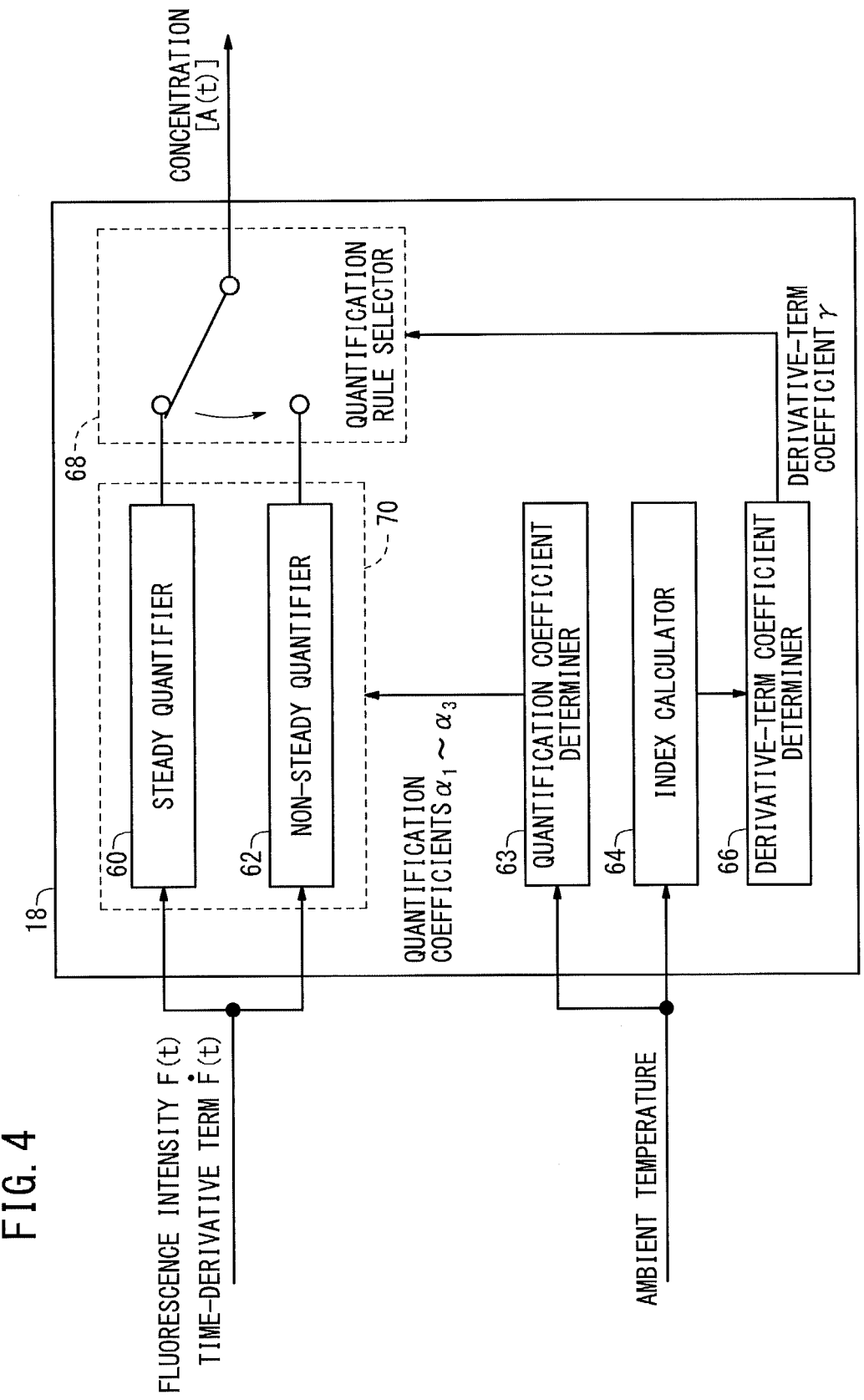
FIG. 4 is a functional block diagram of a processor according to the first embodiment.

As shown in FIG. 4, the processor 18 according to the first embodiment includes a steady quantifier 60 for quantifying the concentration [A(t)] of analytes A according to a steady quantification formula (steady concentration quantification rule), a non-steady quantifier 62 for quantifying the concentration [A(t)] of analytes A according to a non-steady quantification formula (non-steady concentration quantification rule), a quantification coefficient determiner 63, an index calculator 64, a derivative-term coefficient determiner 66, and a quantification rule selector 68 for selecting a concentration quantification formula from the above steady quantification formula, and at least one non-steady quantification formula as the above non-steady quantification formula. The steady quantifier 60 and the non-steady quantifier 62 jointly function as a concentration quantifier 70 for quantifying the concentration [A(t)] of analytes A according to predetermined concentration quantification formulas.

In the present description, the term "steady concentration quantification rule" implies a quantification rule for the concentration [A(t)] in relation to a fluorescence intensity F(t). The steady quantification formula is a form of the steady concentration quantification rule, and represents an equation concerning the concentration [A(t)] in relation to the fluorescence intensity F(t) (specifically, equation (2) discussed above).

The term "non-steady concentration quantification rule" implies a quantification rule for the concentration [A(t)] in relation to a time derivative of a fluorescence intensity F(t) (e.g., a first-order time-derivative term F'(t) or a second- or higher-order time-derivative term). Equation (1), which is an equation concerning a reaction rate in a steady state, may be expanded into the following first-order differential equation (3) with respect to time t:

$$\gamma \dot{F}(t) = -(\alpha_1 [A(t)] + \alpha_2) F(t) + \alpha_3 [A(t)] \quad (3)$$

where $\alpha_1$, $\alpha_2$, $\alpha_3$ represent quantification coefficients for quantifying the concentration [A(t)] of analytes A, and $\gamma$ represents a coefficient (hereinafter referred to as a "derivative-term coefficient") representative of the degree of contribution of the time-derivative term F'(t). For example, the coefficient $\gamma$ may take a value of 0 or a positive real number. In the following description and in the drawings, the first-order time-derivative term F'(t) may occasionally be expressed as a multiplicand term for $\gamma$ on the left side of equation (3). From equation (3), the concentration [A(t)] is calculated as follows:

$$[A(t)] = \frac{\gamma \dot{F}(t) + \alpha_2 F(t)}{\alpha_3 - \alpha_1 F(t)} \quad (4)$$

Equation (4) represents an equation concerning the fluorescence intensity F(t) and the time-derivative term F'(t). If $\gamma$ is non-zero, then equation (4) corresponds to the "non-steady quantification formula" as one form of the non-steady concentration quantification rule. If $\gamma$ is 0, then the right side of equation (4) is the same as the right side of equation (2)

(steady quantification formula). If the concentration [A(t)] cannot be expressed as an exact solution for the fluorescence intensity F(t), then the concentration [A(t)] may be calculated according to a known nonlinear optimization method, a steepest descent method, Newton's method, a quasi-Newton's method, a simplex method, or the like, or may be calculated using a known estimation algorithm including a Karman filter. The same applies to the steady concentration quantification rule.

Figure 5A:
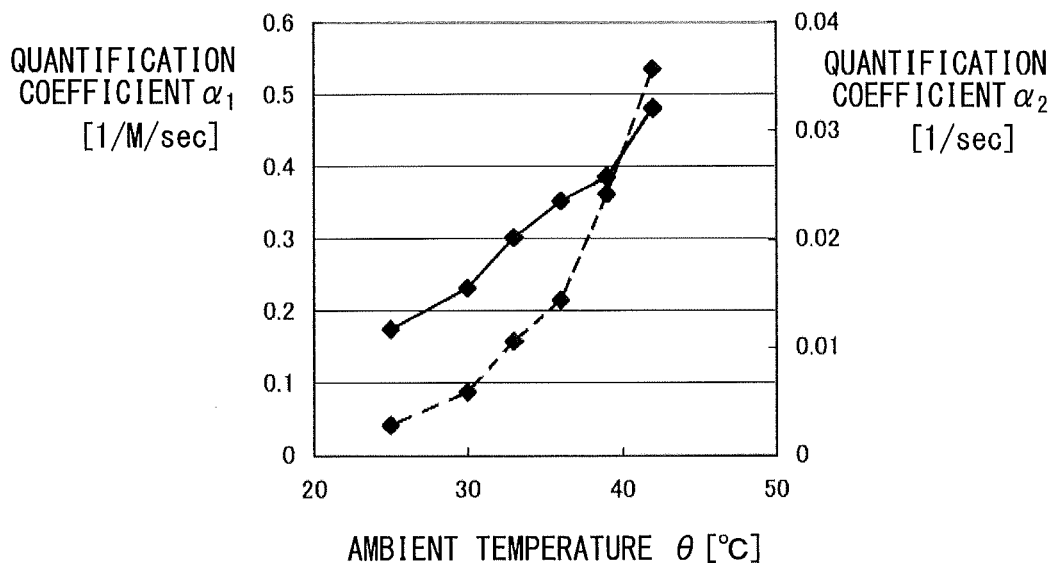
FIGS. 5A and 5B are graphs showing examples of quantification coefficients according to the first embodiment.
Figure 5B:
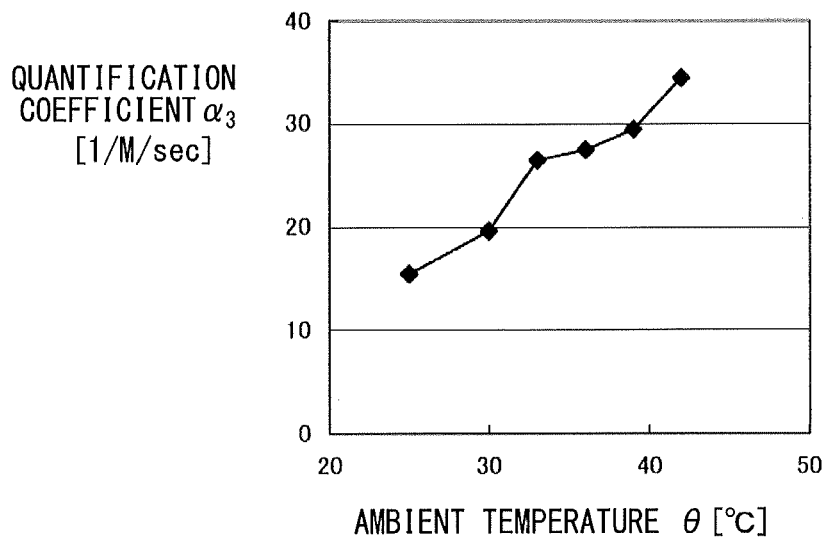

FIGS. 5A and 5B are graphs showing examples by which the quantification coefficients $\alpha_1$ through $\alpha_3$ are determined. Each of the graphs has a horizontal axis representing the ambient temperature $\theta$ (units: ° C.), and a vertical axis representing the quantification coefficient $\alpha_1$ (indicated by the solid-line curve in FIG. 5A, units: $M^{-1}s^{-1}$), the quantification coefficient $\alpha_2$ (indicated by the broken-line curve in FIG. 5A, units: $s^{-1}$), and the quantification coefficient $\alpha_3$ (units: $M^{-1}s^{-1}$). The unit [M] implies a molar concentration [mol/L]. The quantification coefficients $\alpha_1$ through $\alpha_3$, which are suitable for the ambient temperature $\theta$, are determined accordingly.

Figure 6A:
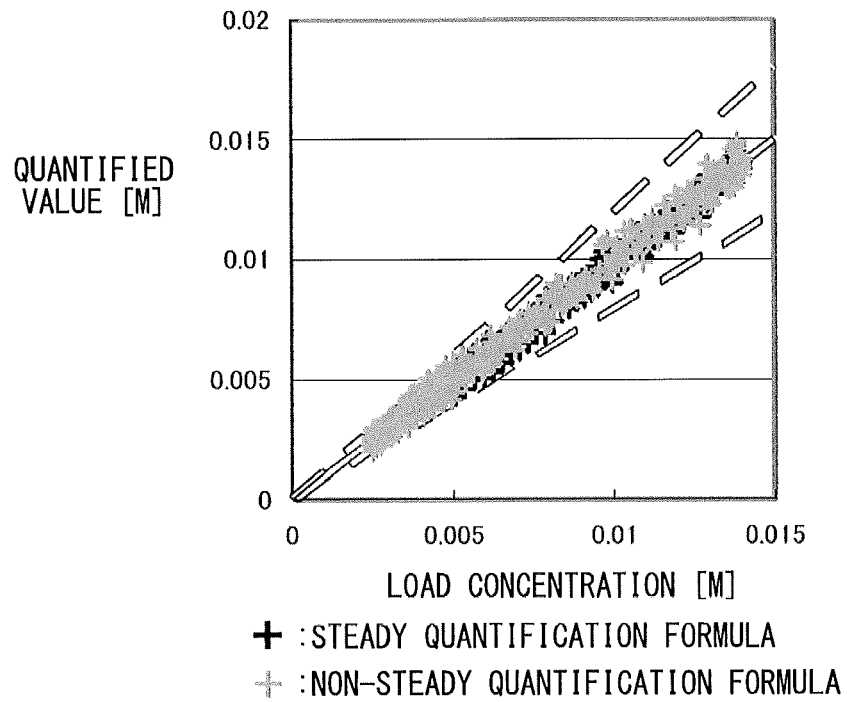
FIGS. 6A and 6B are graphs showing correlations between load concentrations and quantified values at a constant ambient temperature.
Figure 6B:
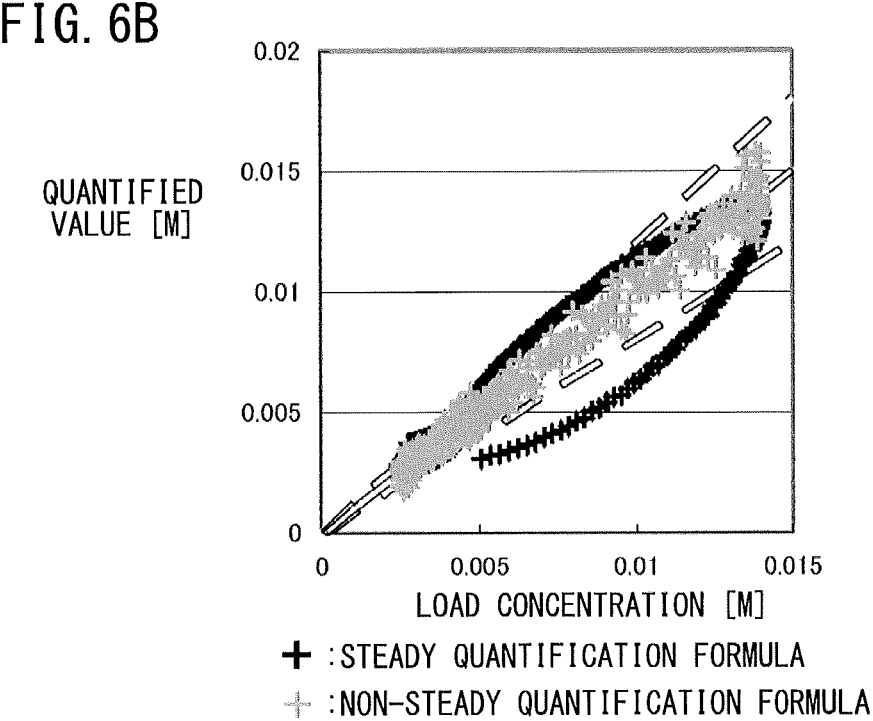

FIGS. 6A and 6B are graphs showing correlations between load concentrations of glucose and quantified values at a constant ambient temperature ($\theta$). Each of the graphs has a horizontal axis representing load concentrations (units: M), and a vertical axis representing quantified values (units: M).

In FIGS. 6A and 6B, if the quantified values are plotted on an equivalent-value straight line (Y=X), then the quantified values represent optimal quantification characteristics. In order to easily judge whether correlations are good or bad, an upper limit value (Y=1.2X) and a lower limit value (Y=0.8X) are indicated as broken-line curves, in order to establish allowable errors within 20% of the optimal values (Y=X). The same also applies to FIGS. 11 and 13, to be described later.

The graph shown in FIG. 6A is plotted at an ambient temperature $\theta$ of 42° C. As shown in FIG. 6A, all of the quantified values produced according to the steady quantification formula ($\gamma=0$) and the non-steady quantification formula ($\gamma=1$) fall essentially within the range of allowable errors. A comparison between the quantified values produced according to the steady quantification formula ($\gamma=0$) and the quantified values produced according to the non-steady quantification formula ($\gamma=1$) indicates that the quantified values according to the steady quantification formula ($\gamma=0$) are of slightly higher quantification accuracy than the quantified values according to the non-steady quantification formula ($\gamma=1$). It is estimated that this is caused because differential errors in fluorescence intensity F(t) are likely to occur when the time-derivative term F'(t) is calculated.

The graph shown in FIG. 6B is plotted at an ambient temperature $\theta$ of 25° C. As shown in FIG. 6B, the quantified values produced according to the non-steady quantification formula ($\gamma=1$) fall essentially within the range of allowable errors (20%), whereas certain ones of the quantified values produced according to the steady quantification formula ($\gamma=0$) fall significantly outside of the range of allowable errors. The reasons as to why the quantified values fall outside of the range of allowable errors will be described below.

In a bond dissociation reaction, the reaction ratio may vary depending on the ambient temperature $\theta$. Generally, the reaction rate tends to be lower at lower temperatures. For example, a fluorescent signal generated from a fluorochrome, as disclosed in Japanese Patent No. 2883824, varies only when the fluorochrome is bonded to and dissociated from low-molecular-weight glucose, so it is expected that the reaction rate essentially is not lowered.

In a reaction in which rhodamine-labeled concanavalin A and fluorescein-labeled dextran are bonded and dissociated, the reaction rate is expected to be lowered significantly, because the molecules that react with each other belong to polymers having large molecular weights, and a reaction to dissociate rhodamine-labeled concanavalin A and fluorescein-labeled dextran from each other is required before the analytes A and the labeled compound are bonded together.

If a bond dissociation reaction is delayed, then a fluorescence intensity F(t) having a stationary value depending on the actual concentration [A(t)] of analytes A cannot immediately be acquired, resulting in a substantial quantification error. For this reason, according to a steady quantification rule, which takes into account only the fluorescence intensity F(t), the quantification accuracy at low ambient temperatures $\theta$ is relatively low. However, according to a steady quantification rule, which takes into account not only the fluorescence intensity F(t) but also a time-depending change in the fluorescence intensity F(t), the quantification accuracy at low ambient temperatures $\theta$ is relatively high.

A relationship between the quantification model represented by equation (2) and a quantification error will be described in specific detail below. According to the results of a study conducted by the present inventor, it has been found that the quantification accuracy according to equation (2) varies depending on a relative magnitude relationship between a time-dependent change in the fluorescence intensity F(t) and $\alpha_2 F(t)$, which serves as the numerator of equation (2). For example, if $\alpha_2 F(t)$ is relatively large to a sufficient degree, then the quantification accuracy of the concentration [A(t)] is good.

However, if $\alpha_2 F(t)$ is small, then the quantified value of the concentration [A(t)] suffers a time delay if the time-dependent change in the fluorescence intensity F(t) is steep. As a result, the quantification accuracy according to equation (2) is reduced. Such a problem manifests itself when the concentration [A(t)] is low, i.e., the fluorescence intensity F(t) is small, and when the ambient temperature $\theta$ is low, i.e., the quantification coefficient $\alpha_2$ is small. In particular, if glucose is used as an analyte A, then the quantification accuracy in a low body temperature state and a low blood sugar state, which are especially required for the analysis of time-series data of the quantified values of the concentration [A(t)], i.e., blood sugar levels, is lowered, which is undesirable.

To solve the above problems, according to the first embodiment, a process is proposed for selecting the steady quantification formula and the non-steady quantification formula. Referring back to FIG. 4, the quantification rule selector 68 selects a concentration quantification formula from among the steady quantification formula ($\gamma=0$) and the non-steady quantification formula ($\gamma \neq 0$). Operations of the components, which are involved in the selection of a concentration quantification formula, i.e., the index calculator 64 and the derivative-term coefficient determiner 66, will be described later.

Figure 7:
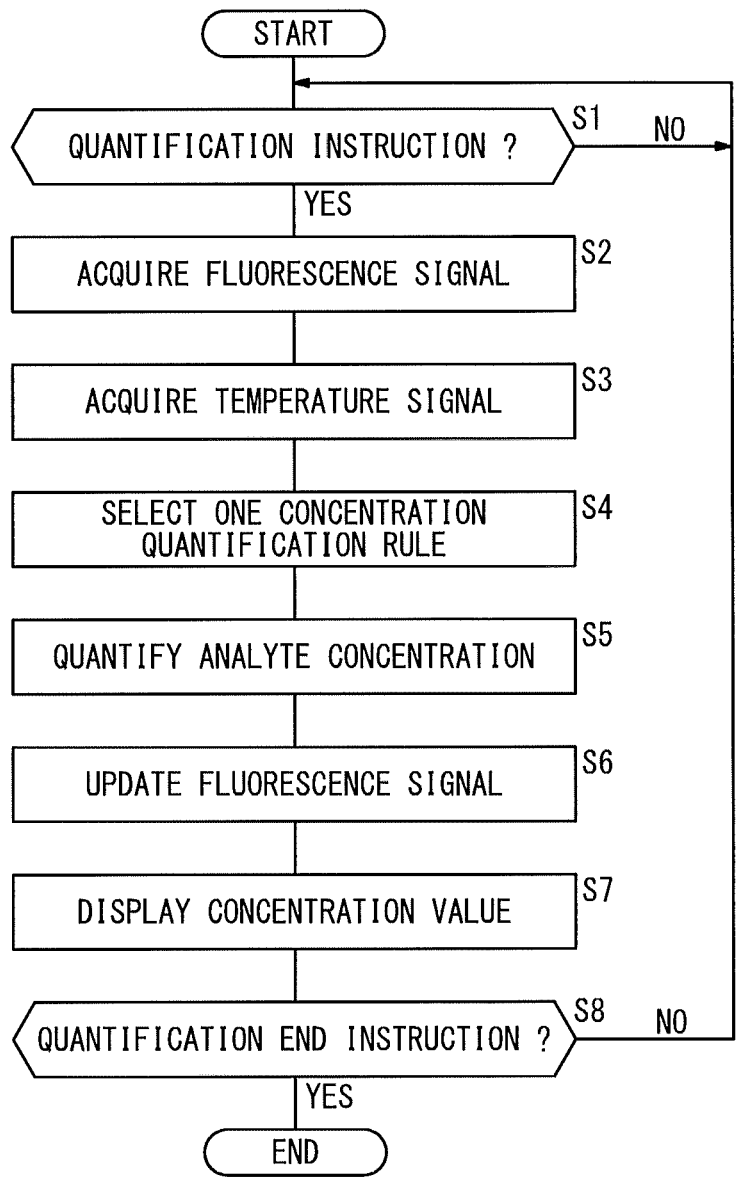
FIG. 7 is a flowchart of an operation sequence of the sensing device incorporating the processor shown in FIG. 4.

Operations of the sensing device 10, which incorporates the processor 18, will be described below with reference to the flowchart shown in FIG. 7 and the block diagrams shown in FIGS. 1 and 4.

In step S1, the processor 18 judges whether or not there is an instruction to quantify analytes A. More specifically, the processor 18 counts the number of pulses of a clock signal, which is input from the clock generator 26. If the counted number of pulses reaches an upper limit count value, which corresponds to a sampling interval Ts upon conversion thereof into time, then the processor 18 judges that there is an instruction to quantify analytes A. If the counted number of pulses does not reach the upper limit count value, then control remains at step S1 until the counted number of pulses reaches the upper limit count value. The quantification time is represented by t.

In step S2, the sensor control circuit 16 detects, with the fluorescence sensor 14, a fluorescence F (see FIG. 3) emitted due to an interaction between analytes A and a labeled compound. The sensor control circuit 16 acquires a fluorescence signal depending on the intensity of the fluorescence F, and supplies the acquired fluorescence signal to the processor 18. The processor 18 converts the fluorescence signal into a fluorescence intensity F(t), or maintains the value of the fluorescence signal as is, and temporarily stores the fluorescence intensity F(t) or the fluorescence signal in the RAM 24.

In step S3, the sensor control circuit 16 acquires, by way of the temperature sensor 15, a temperature signal depending on the ambient temperature θ, and supplies the acquired temperature to the processor 18. The processor 18 converts the temperature signal into an ambient temperature θ, or maintains the value of the temperature signal as is, and temporarily stores the ambient temperature θ or the temperature signal in the RAM 24.

In step S4, the quantification rule selector 68 selects a concentration quantification formula from among the steady quantification formula (γ=0) and the non-steady quantification formula (γ=1). A process for selecting a concentration quantification formula will be described in detail below.

Using the ambient temperature β read from the RAM 24, the index calculator 64 calculates an index $\beta_1$ for determining a derivative-term coefficient γ. For example, the index $\beta_1$ is expressed using the ambient temperature θ according to the following equation (5):

$$\beta_1 = \theta \quad (5)$$

The index $\beta_1$ represents the ambient temperature θ itself. Thereafter, using the index $\beta_1$ acquired from the index calculator 64, the derivative-term coefficient determiner 66 determines a derivative-term coefficient γ.

Figure 8:
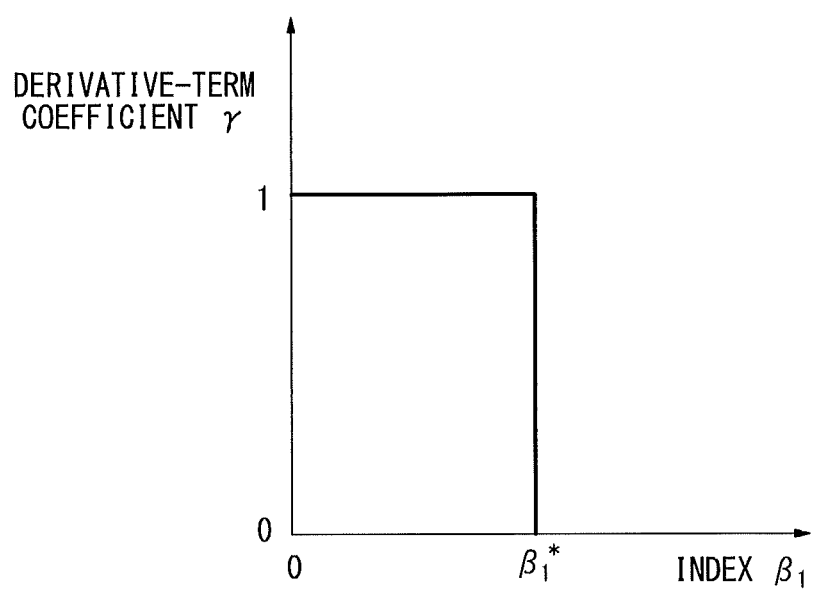
FIG. 8 is a graph showing an example in which a derivative-term coefficient according to the first embodiment is determined.

FIG. 8 is a graph showing an example in which a derivative-term coefficient γ is determined according to the first embodiment. According to the graph, the derivative-term coefficient γ is expressed by a step function, which takes two values with a first threshold value $\beta_1^*$ serving as a boundary. More specifically, if $\beta_1 \leq \beta_1^*$, then the derivative-term coefficient γ is γ=1 (non-steady quantification formula), and if $\beta_1 > \beta_1^*$, then the derivative-term coefficient γ is γ=0 (steady quantification formula).

The quantification rule selector 68 selects one of the steady quantifier 60 (γ=0) and the non-steady quantifier 62 (γ=1), depending on the derivative-term coefficient γ acquired from the derivative-term coefficient determiner 66. As can be understood from the tendency of the quantification accuracy shown in FIGS. 6A and 6B and the graph characteristics shown in FIG. 8, the quantification rule selector 68 selects a concentration quantification formula for enabling higher quantification accuracy depending on a change in the ambient temperature θ.

In step S5, the steady quantifier 60 (or the non-steady quantifier 62) quantifies the concentration [A(t)] of analytes A. Before the concentration [A(t)] is quantified, the quantification coefficient determiner 63 determines quantification coefficients $\alpha_1$ through $\alpha_3$, and supplies the determined quantification coefficients $\alpha_1$ through $\alpha_3$ to the concentration quantifier 70. More specifically, the quantification coefficient determiner 63 successively determines quantification coefficients $\alpha_1$ through $\alpha_3$ based on the ambient temperature θ acquired from the temperature sensor 15. For example, if the quantification coefficients $\alpha_1$ through $\alpha_3$ (see FIGS. 5A and 5B) are maintained in the form of a table, the quantification coefficient determiner 63 determines the quantification coefficients $\alpha_1$ through $\alpha_3$ depending on the ambient temperature θ, according to a known interpolation or extrapolation process.

The quantification coefficient determiner 63 may alternatively determine quantification coefficients $\alpha_1$ through $\alpha_3$ according to a predetermined approximation function, which is produced from plotted values at respective ambient temperatures θ. The approximation function may be represented by any of various equations, including polynomials such as an exponential function, a cubic function, etc. It is convenient to predetermine various coefficients for identifying the form of the function for the quantification coefficients $\alpha_1$ through $\alpha_3$, since a smaller amount of data is involved than if the quantification coefficients $\alpha_1$ through $\alpha_3$ were maintained in the form of a table.

Thereafter, using the fluorescence intensity F(t) and the time-derivative term F'(t) read from the RAM 24, the steady quantifier 60 (or the non-steady quantifier 62) quantifies the concentration [A(t)] according to the concentration quantification rule represented by equation (2) or (4). The time-derivative term F'(t) may be acquired from a filter circuit included in the sensor control circuit 16, or may be calculated from past or preexisting data of the fluorescence intensity F(t) stored in the RAM 24.

In step S6, the processor 18 stores in the RAM 24 the fluorescence intensity F(t) and the time-derivative term F'(t) acquired at the quantification time t, thereby updating the data stored in the RAM 24.

In step S7, the processor 18 displays on the display unit 28 various items of information concerning the concentration [A(t)] quantified in step S5.

In step S8, the processor 18 judges whether or not there is an instruction to end the above quantification sequence. If the processor 18 judges that an instruction does not exist to end the quantification sequence, then control returns to step S1, and steps S1 through S7 are repeated. If the processor 18 judges that there is an instruction to end the quantification sequence, then the sensing device 10 brings the process of quantifying analytes A to an end.

Thus, concentrations [A(t)] of analytes A at respective quantification times t are acquired as time-series data. The accuracy of quantification achieved using the sensing method according to the present invention will be described below.

Figure 9:
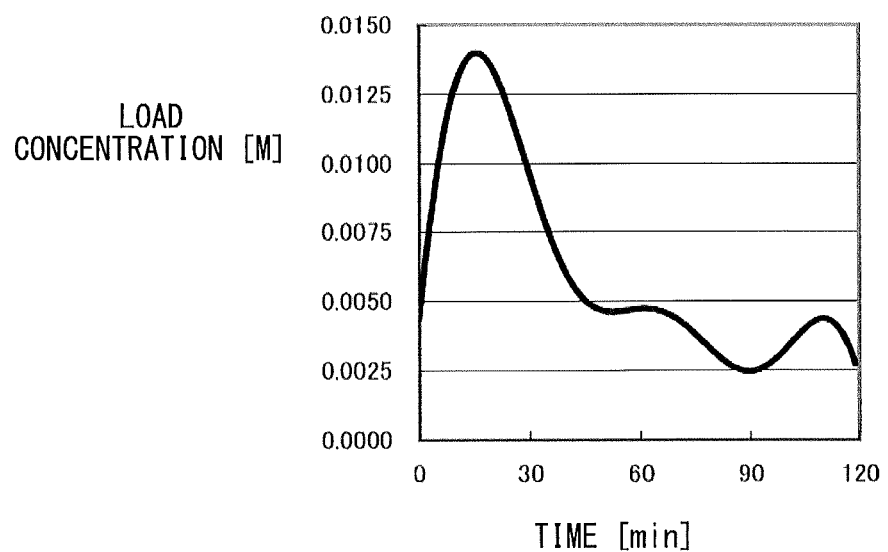
FIG. 9 is a graph showing time-dependent changes in a load concentration of glucose.

FIG. 9 is a graph showing time-dependent changes in the load concentration of glucose. The graph has a horizontal axis representing time (units: min) and a vertical axis representing load concentrations of glucose (units: M). Changes in the concentration simulate time-dependent changes in the load concentration of glucose in the body of an examinee after the examinee has eaten a meal.

Figure 10:
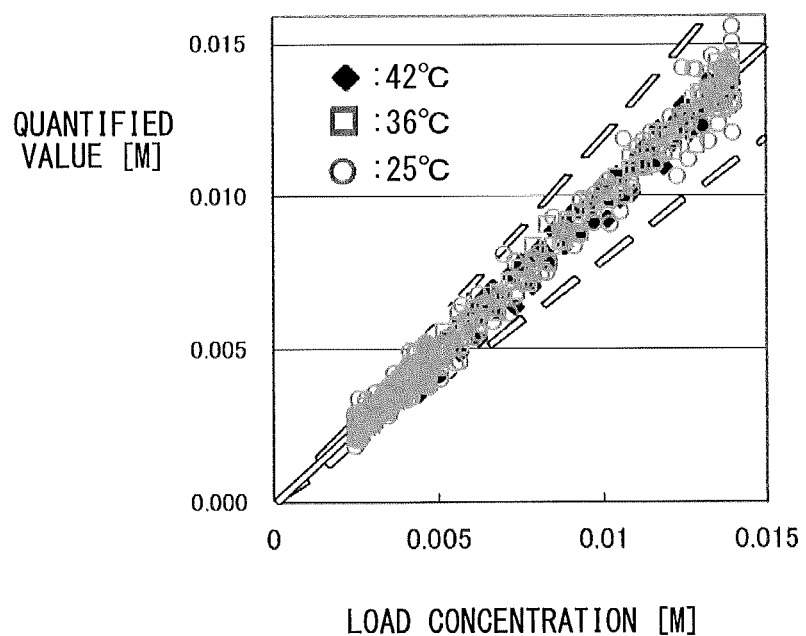
FIG. 10 is a graph showing a correlation between load concentrations of glucose and quantified values in accordance with a derivative-term coefficient determined according to a first modification.

FIG. 10 is a graph showing a correlation between load concentrations of glucose and quantified values at each of separate ambient temperatures θ. The graph shows load concentrations and quantified values plotted for a case in which the glucose concentration is quantified successively at a sampling interval of Ts=30 (s), as the concentration varies as shown in FIG. 9. The load concentrations are plotted at three ambient temperatures θ=42° C., 36° C., 25° C. As shown in FIG. 10, the quantified values essentially fall within an allowable range (with an error of 20%) around the optimal values (Y=X) at the three ambient temperatures θ. The sensing method according to the present invention achieves higher quantification accuracy than if either one of the steady quantification formula and the non-steady quantification formula were applied (see FIGS. 6A and 6B), even if the ambient temperature θ varies in a range from 25° C. to 42° C.

As described above, the processor 18 includes the fluorescence sensor 14, which acquires a fluorescence intensity F(t) at a predetermined quantification time t, the steady quantifier 60, which quantifies the concentration [A(t)] of analytes A according to the steady quantification formula concerning the fluorescence intensity F(t), the non-steady quantifier 62, which quantifies the concentration [A(t)] of analytes A according to the non-steady quantification formula representative of the relationship between the fluorescence intensity F(t) and the time-derivative term F'(t), and the quantification rule selector 68, which selects a concentration quantification formula from among the steady quantification formula and the non-steady quantification formula depending on the ambient temperature θ. Since a concentration quantification formula can be selected that is suitable for the tendency of time-dependent changes in the fluorescence intensity F(t), the concentration [A(t)] of analytes A can be quantified highly accurately regardless of the measuring environment.

The quantification rule selector 68 selects a steady concentration quantification rule if the ambient temperature θ exceeds the first threshold value $\beta_1^*$, and selects a non-steady concentration quantification rule if the ambient temperature θ does not exceed the first threshold value $\beta_1^*$. Therefore, even if time-dependent changes in the fluorescence intensity F(t) are relatively steep compared with the response rate at which fluorescence F is emitted, such changes are immediately reflected in the quantified value of the concentration [A(t)], thereby resulting in highly accurate quantified results.

Modifications (first through third modifications) of the first embodiment will be described below with reference to FIGS. 11A through 13B.

First Embodiment

First Modification

According to a first modification, an index ($\beta_2$) for determining a derivative-term coefficient γ differs from the index $\beta_1$ according to the first embodiment. The index calculator 64 calculates an index $\beta_2$ for determining the derivative-term coefficient γ, using the fluorescence intensity F(t) and the time-derivative term F'(t) read from the RAM 24. For example, the index $\beta_2$ is expressed by the following equation (6):

$$\beta_2 = \left|\frac{\dot{F}(t)}{F(t)}\right| = \left|\frac{\partial(\ln|F(t)|)}{\partial t}\right| \qquad (6)$$

The index $\beta_2$ corresponds to a time rate of change of fluorescence intensity F(t). Thereafter, using the index $\beta_2$ acquired from the index calculator 64, the derivative-term coefficient determiner 66 determines a derivative-term coefficient γ. The index $\beta_2$ is not limited to a time rate of change of fluorescence intensity F(t), but may be an index corresponding to a time-dependent change, e.g., the absolute value |F'(t)| of the time-derivative term.

Figure 11A:
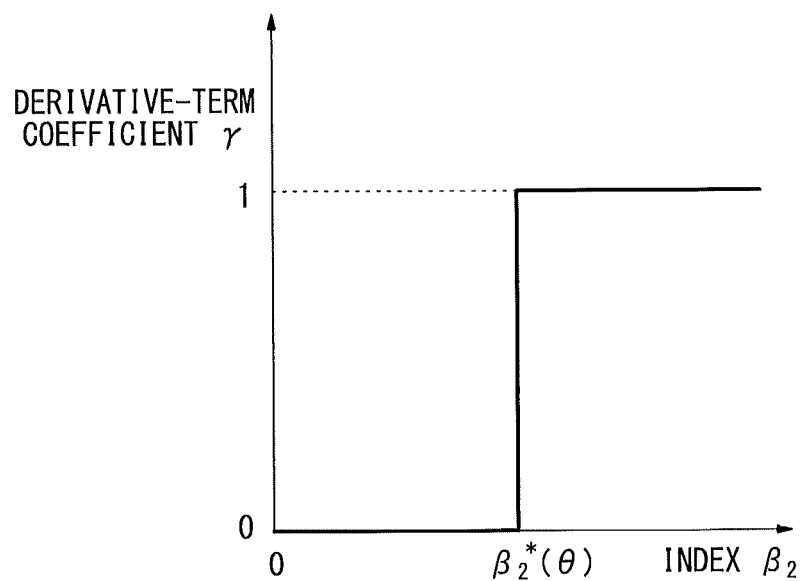
FIG. 11A is a graph showing an example in which the derivative-term coefficient according to the first modification is determined.
Figure 11B:
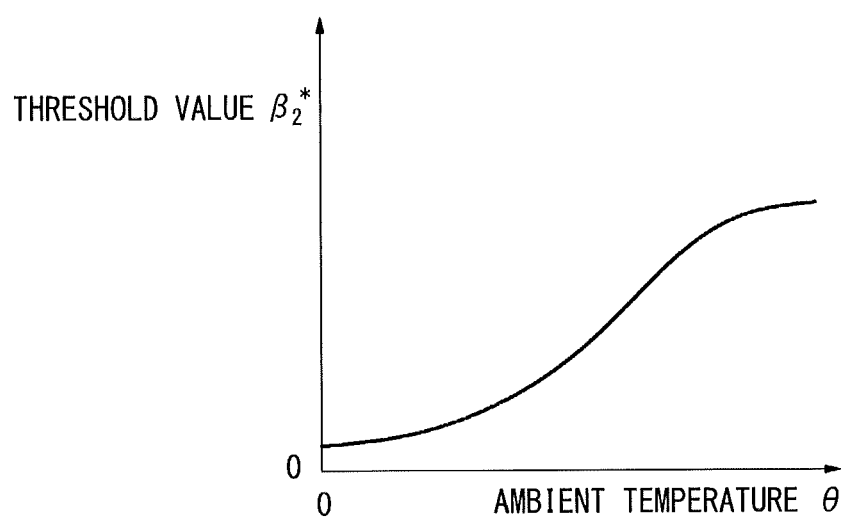
FIG. 11B is a graph illustrative of an example in which a second threshold value shown in FIG. 11A is determined.

FIGS. 11A and 11B are graphs illustrative of an example in which the derivative-term coefficient γ according to the first modification is determined.

As shown in FIG. 11A, the derivative-term coefficient γ is expressed by a step function, which takes two values with a second threshold value $\beta_2^*$ serving as a boundary. More specifically, if $\beta_2 \leq \beta_2^*(\theta)$, then the derivative-term coefficient γ is γ=0 (steady quantification formula), and if $\beta_2 > \beta_2^*(\theta)$, then the derivative-term coefficient γ is γ=1 (non-steady quantification formula). If the second threshold value $\beta_2^*(\theta)$ is constant, then 0 is more easily selected as the derivative-term coefficient γ, as the time rate of change of fluorescence intensity F(t) is smaller, or as the rate of the bonding dissociation reaction is lower.

As shown in FIG. 11B, the second threshold value $\beta_2^*(\theta)$ is determined depending on the ambient temperature θ. As shown in the graph, as the ambient temperature θ increases, the second threshold value $\beta_2^*(\theta)$ increases nonlinearly. In other words, as the ambient temperature θ increases, 0 is more easily selected as the derivative-term coefficient γ.

Figure 12:
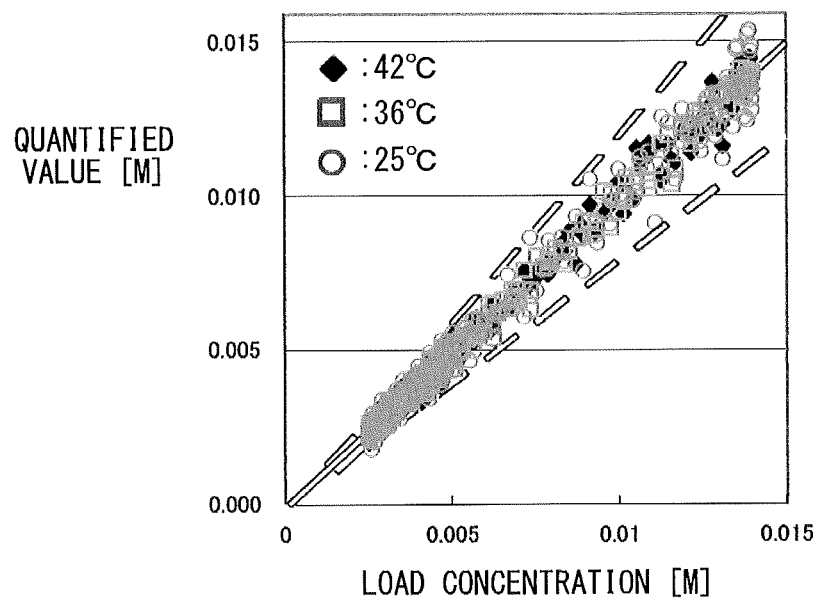
FIG. 12 is a graph showing a correlation between load concentrations of glucose and quantified values in accordance with the derivative-term coefficient determined according to the first modification.

FIG. 12 is a graph showing a correlation between load concentrations of glucose and quantified values according to the derivative-term coefficient γ according to the first modification. According to the first modification, correlation characteristics, which are essentially the same as those according to the first embodiment (see FIG. 10), are obtained using the index $\beta_2$.

As described above, the quantification rule selector 68 selects a steady concentration quantification rule if the index $\beta_2$ (the time-dependent change in the fluorescence intensity F(t)) does not exceed the second threshold value $\beta_2^*$, and selects a non-steady concentration quantification rule if the index $\beta_2$ exceeds the second threshold value $\beta_2^*$, thereby offering the same advantages as those according to the first embodiment. The derivative-term coefficient determiner 66 may determine a derivative-term coefficient γ using the index $\beta_1$ and the index $\beta_2$.

First Embodiment

Second Modification

According to a second modification, the form of the function for determining a derivative-term coefficient γ differs from the form of the function according to the first embodiment (see FIG. 8). Using the index $\beta_1$ ($\beta_2$) acquired from the index calculator 64, the derivative-term coefficient determiner 66 determines a derivative-term coefficient γ.

Figure 13A:
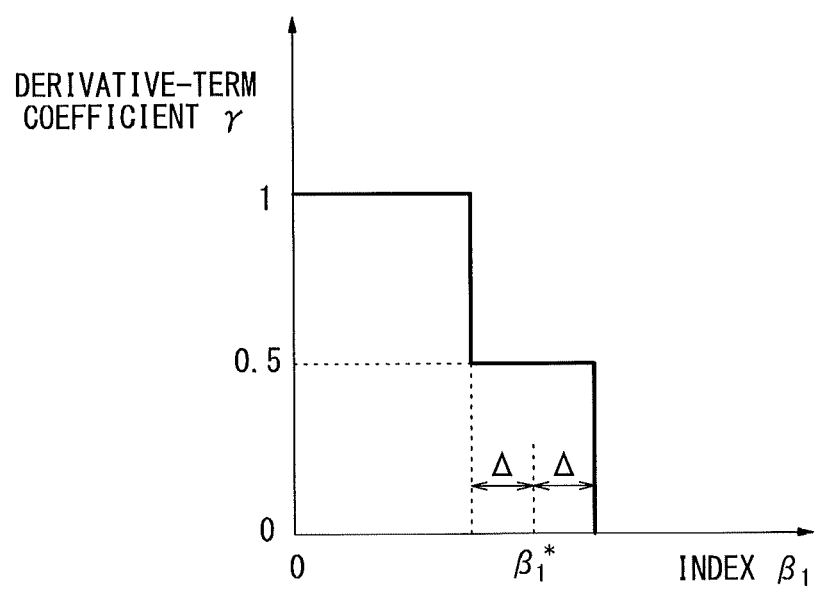
FIGS. 13A and 13B are graphs showing an example in which a derivative-term coefficient according to a second modification is determined.

FIG. 13A is a graph illustrative of an example in which a derivative-term coefficient γ is determined according to the second modification. In the graph, the derivative-term coefficient γ is expressed by a step function, which takes three values. More specifically, if $\beta_1 < (\beta_1^* - \Delta)$, then the derivative-term coefficient γ is γ=1 (non-steady quantification formula), if $(\beta_1^* - \Delta) \leq \beta_1 \leq (\beta_1^* + \Delta)$, then the derivative-term coefficient γ is γ=0.5 (non-steady quantification formula), and if $\beta_1 > (\beta_1^* + \Delta)$, then the derivative-term coefficient γ is γ=0 (steady quantification formula). As described above, the quantification rule selector 68 may select a concentration quantification formula from among one steady quantification formula and a plurality of non-steady quantification formulas.

Figure 13B:
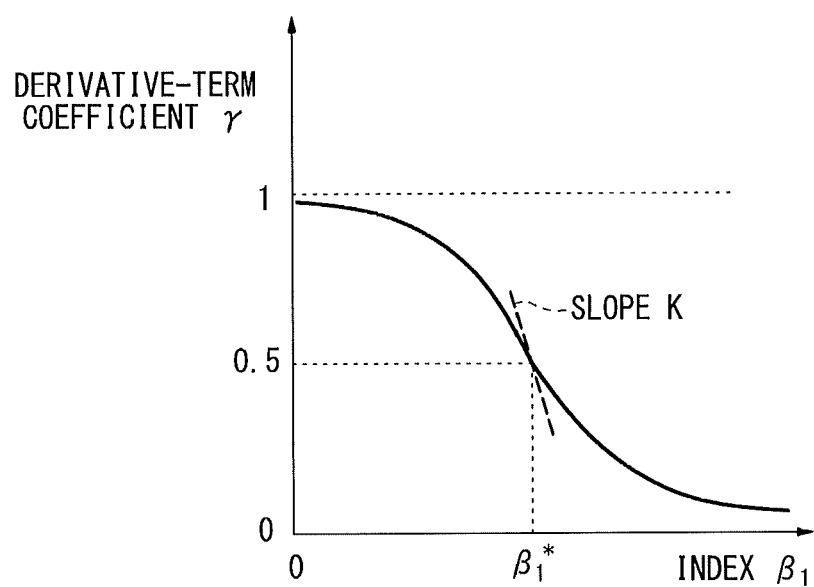

FIG. 13B is a graph illustrative of another example in which a derivative-term coefficient γ according to a second modification is determined. In the graph, the derivative-term coefficient γ is expressed by a continuous function (sigmoidal function), which is represented by the following equation (7):

$$\gamma = 1/[1 + \exp\{K(\beta_1 - \beta_1^*)\}] \qquad (7)$$

where K is a coefficient corresponding to the gradient of a curve at the coordinates $\beta_1 = \beta_1^*$. If the value of K is sufficiently large (nearly infinite), then the function that expresses the derivative-term coefficient γ is consistent in shape with the step function shown in FIG. 8. Thus, the quantification rule selector 68 may select a concentration quantification formula from among several non-steady quantification formulas expressed by a continuous function, etc., via parameters. If the index $\beta_1$ in equation (7) is sufficiently large, then since the derivative-term coefficient $\gamma$ is extremely small, quantified results are obtained, which are essentially the same as those of the steady quantification formula ($\gamma$=0).

By changing the derivative-term coefficient $\gamma$ (i.e., the degree of contribution of the time-derivative term F'(t)) in a stepwise manner, it is possible to reduce discontinuity in the quantified values owing to differently selected concentration quantification rules, particularly in the vicinity of the first threshold value $\beta_1^*$, thereby avoiding the risk of localized reductions in quantification accuracy.

The index $\beta_2$ (see FIG. 11A) may be defined according to the form of the function shown in FIG. 13A (or FIG. 13B). In this case, the same advantages as those of the first embodiment can be achieved, assuming that the quantification rule selector 68 increases the derivative-term coefficient $\gamma$ as the ambient temperature $\theta$ is lowered and/or reduces the derivative-term coefficient $\gamma$ as the ambient temperature $\theta$ rises.

First Embodiment

Third Modification

According to the third modification, a process of determining the derivative-term coefficient $\gamma$ differs from the process according to the first embodiment (see FIG. 8). The derivative-term coefficient determiner 66 calculates a probability using the index $\beta_1$ ($\beta_2$), which is acquired from the index calculator 64, and determines a derivative-term coefficient $\gamma$ according to such a probability. For example, the derivative-term coefficient determiner 66 may calculate a probability according to the following equation (8):

$$\text{Prob}(\gamma=1)=1/[1+\exp\{+K(\beta_1-\beta_1^*)\}]$$

$$\text{Prob}(\gamma=0)=1/[1+\exp\{-K(\beta_1-\beta_1^*)\}]$$

The derivative-term coefficient determiner 66 may determine the value of a derivative-term coefficient $\gamma$ probabilistically, based on a random number generated using an algorithm for generating a pseudorandom number. By selecting a derivative-term coefficient $\gamma$ according to the probability expressed by equation (8), the expected value of the derivative-term coefficient $\gamma$ is equivalent to the graph characteristics shown in FIG. 13B.

Second Embodiment

A sensing method according to a second embodiment of the present invention will be described below with reference to FIGS. 14 through 18. Components according to the second embodiment, which are identical to those according to the first embodiment, will be denoted by identical reference characters, and such features will not be described in detail below.

Figure 14:
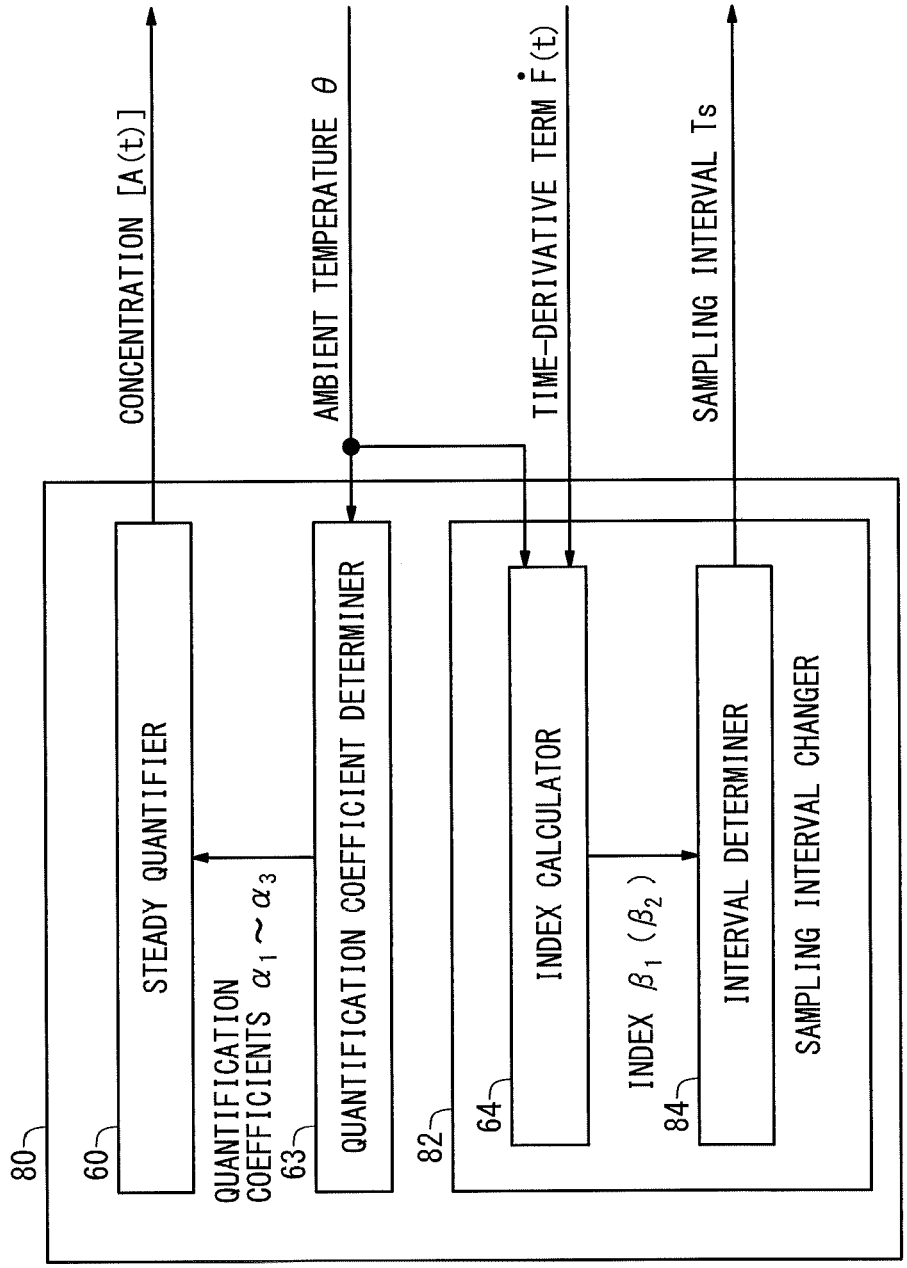
FIG. 14 is a functional block diagram of a processor according to the second embodiment.

FIG. 14 is a functional block diagram of a processor 80 according to the second embodiment.

The processor 80 includes a steady quantifier 60 and a quantification coefficient determiner 63, which have the same functions as those according to the first embodiment (see FIG. 4), and a sampling interval changer 82 for changing a sampling interval Ts at which the concentration [A(t)] of analytes A is quantified. The sampling interval changer 82 has an index calculator 64, which has the same function as that according to the first embodiment, and an interval determiner 84 for determining a sampling interval Ts from the index $\beta_1$ ($\beta_2$) that is calculated by the index calculator 64.

Figure 15:
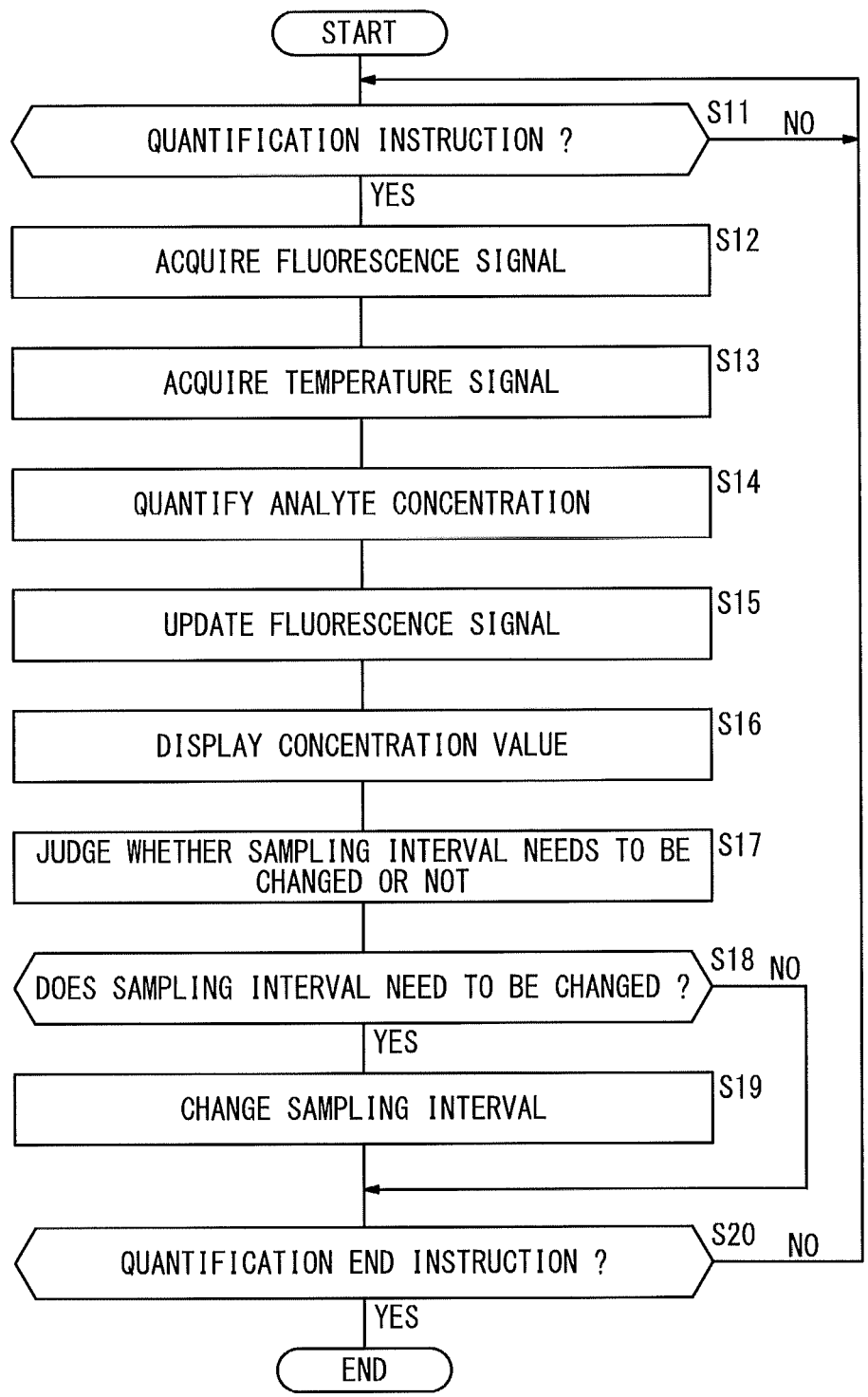
FIG. 15 is a flowchart of an operation sequence of the sensing device incorporating the processor shown in FIG. 14.

Operations of the sensing device 10, which incorporates the processor 80, will be described below with reference to the flowchart shown in FIG. 15. Operational details, which are identical to those according to the first embodiment (see FIG. 7), will not be described below.

Steps S11 through S16 are the same as steps S1 through S3 and S5 through S7 according to the first embodiment (see FIG. 7) and will not be described below. In step S14, the steady quantifier 60 quantifies the concentration [A(t)] according to the steady quantification formula ($\gamma$=0).

In step S17, the sampling interval changer 82 judges whether or not the sampling interval Ts needs to be changed. Prior to making such a judgment, the index calculator 64 calculates an index $\beta_1$ (or $\beta_2$) using the ambient temperature $\theta$, the fluorescence intensity F(t), and the time-derivative term F'(t), which are read from the RAM 24. The indexes $\beta_1$, $\beta_2$ may be identical to or differ from those of the first embodiment and the modifications thereof.

Thereafter, the sampling interval determiner 84 determines a sampling interval Ts from the indexes $\beta_1$, $\beta_2$ acquired from the index calculator 64.

Figure 16A:
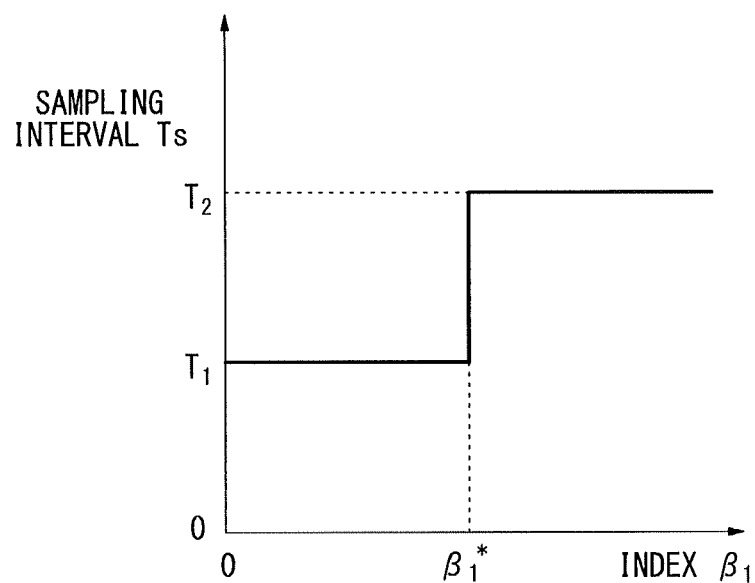
FIGS. 16A and 16B are graphs showing examples in which a sampling interval is determined.

FIG. 16A is a graph illustrative of an example in which a sampling interval Ts is determined according to the second embodiment. As shown in FIG. 16A, a sampling interval Ts is determined depending on the index $\beta_1$. More specifically, a sampling interval Ts is determined as Ts=$T_1$ if $\beta_1<\beta_1^*$, and as Ts=$T_2$ (>$T_1$) if $\beta_1 \geq \beta_1^*$.

Figure 16B:
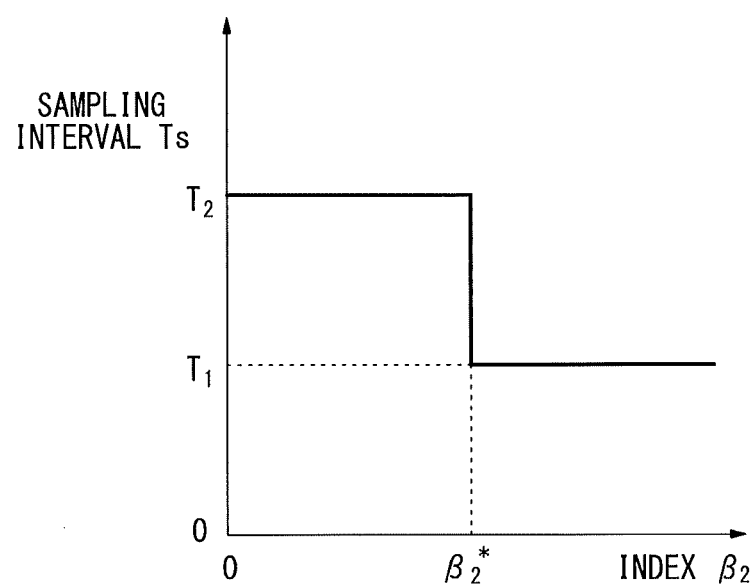

FIG. 16B is a graph illustrative of another example in which a sampling interval Ts is determined according to the second embodiment. As shown in FIG. 16B, a sampling interval Ts is determined depending on the index $\beta_2$. More specifically, a sampling interval Ts is determined as Ts=$T_2$ if $\beta_2<\beta_2^*$, and as Ts=$T_1$ (<$T_2$) if $\beta_2 \geq \beta_2^*$.

Figure 17:
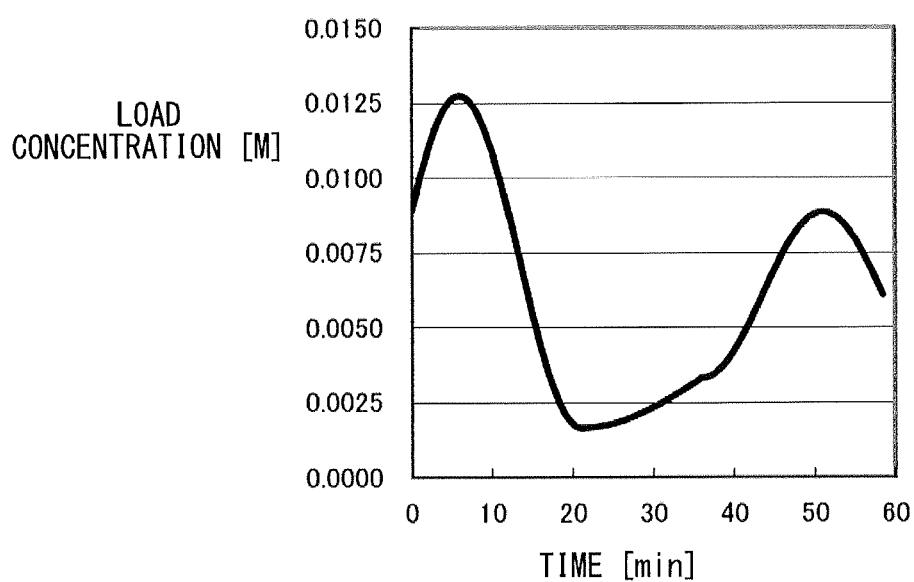
FIG. 17 is a graph showing time-dependent changes in a load concentration of glucose.

FIG. 17 is a graph showing time-dependent changes in the load concentration of glucose. As shown in FIG. 17, the load concentration varies within a slightly greater range than the load concentration shown in FIG. 9.

Figure 18:
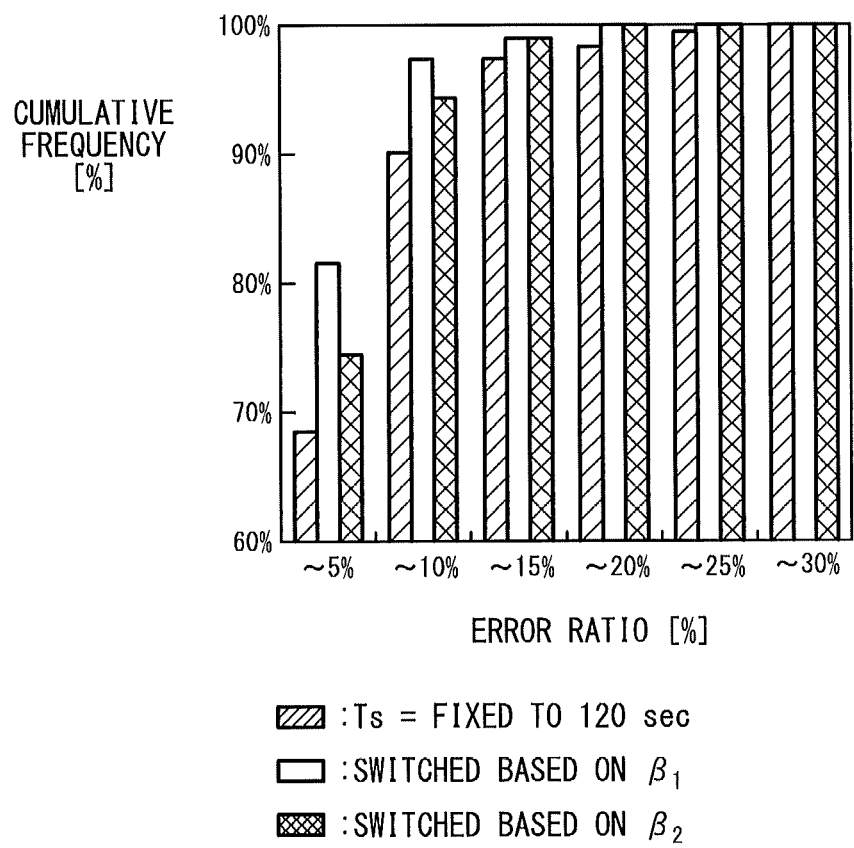
FIG. 18 is a cumulative histogram of glucose quantification error ratios, at times that glucose is quantified according to three sampling interval changing rules.

FIG. 18 is a cumulative histogram of glucose quantification error ratios at times that glucose is quantified according to three sampling interval changing rules. The histogram has a horizontal axis representing error ratios of quantified values (units: %) and a vertical axis representing cumulative frequencies.

According to a first changing rule (fixed to 120 seconds), the sampling interval Ts is set to Ts=120 seconds at all times. According to a second changing rule (switched based on $\beta_1$), the sampling interval Ts is changed according to the example shown in FIG. 16A. According to a third changing rule (switched based on $\beta_2$), the sampling interval Ts is changed according to the example shown in FIG. 16B. The threshold values include the first threshold value $\beta_1^*$=40(° C.) and the second threshold value $\beta_2^*$=0.005. In FIGS. 16A and 16B, $T_1$=60 s and $T_2$=120 s.

As shown in FIG. 18, frequencies at an error ratio of 5% or smaller are progressively higher in the following order: (second changing rule)>(third changing rule)>(first changing rule). Frequencies at an error ratio of 20% or smaller are 100% in accordance with the second and third changing rules, wherein all the quantified values fall within the errors of 20% or smaller. Statistically, therefore, the quantification errors are smaller in the order of the second changing rule, the third changing rule, and the first changing rule.

The sampling interval changer 82 is capable of both maintaining the quantification accuracy and of lowering electric power consumption by appropriately changing the sampling interval Ts at which the fluorescence intensity F(t) is sampled, depending on the time-dependent change in the fluorescence intensity F(t) and/or the ambient temperature θ. If the sampling interval Ts is set to a longer value as required, then the number of times that the excited light E is applied is reduced, thereby preventing the fluorescence sensor 14 from becoming deteriorated.

Third Embodiment

A sensing method according to a third embodiment of the present invention will be described below with reference to FIGS. 19 through 24. Components according to the third embodiment, which are identical to those according to the first embodiment, will be denoted by identical reference characters, and such features will not be described in detail below.

Figure 19:
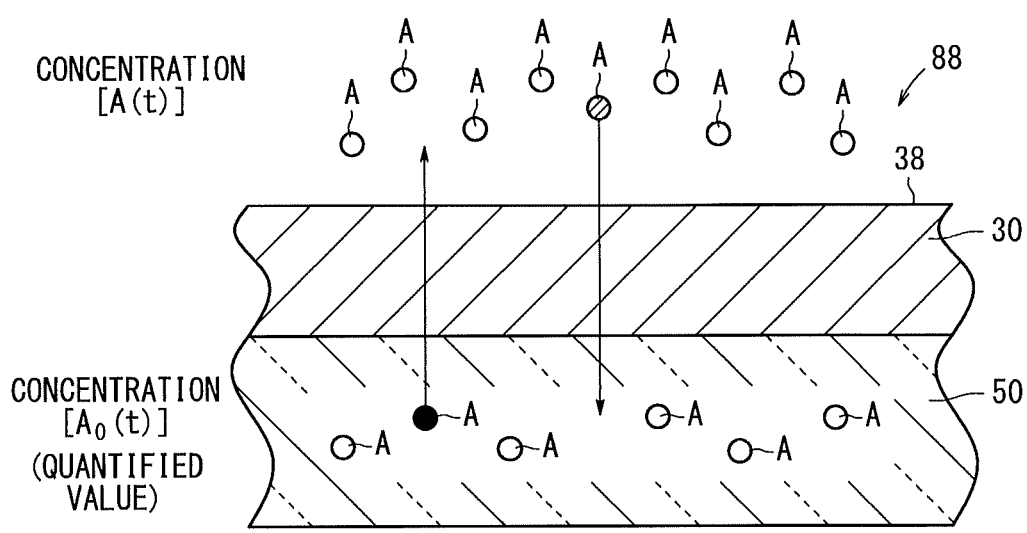
FIG. 19 is a schematic view showing the manner in which analytes permeate an indicator layer.

FIG. 19 is a schematic view showing the manner in which analytes A permeate the indicator layer. More specifically, FIG. 19 is an enlarged fragmentary view of the cross-sectional structure shown in FIG. 2.

A number of analytes A are present in an external region 88 outside of the fluorescence sensor 14. An analyte A (shown in hatching), which is present in the vicinity of the housing 30, penetrates from the entry surface 38 through the housing 30 and into the indicator layer 50 by way of osmosis. An analyte A (shown filled) that is present in the indicator layer 50 penetrates through the housing 30 into the external region 88 from the entry surface 38. The concentration (quantification time t) of the analytes A in the external region 88 will hereinafter be referred to as [A(t)]. The concentration (quantification time t) of the analytes A in the indicator layer 50 will hereinafter be referred to as $[A_0(t)]$.

When triggered by application of the excited light E (see FIG. 3), the indicator layer 50 emits fluorescence F depending on the concentration $[A_0(t)]$ of the analytes A in the indicator layer 50. According to the present embodiment, in order to clearly distinguish from the concentration [A(t)], which is an optimum object to be quantified, the actual quantified concentration $[A_0(t)]$ may be referred to as a "quantified value". The relationship between the concentration [A(t)] and the quantified value $[A_0(t)]$ is expressed according to the following equation (9):

$$[\dot{A}_0(t)] = -\delta\{[A_0(t)] - [A(t)]\} \quad (9)$$

where δ represents an osmosis coefficient of the analytes A with respect to the housing 30, and which is dependent on the combination of the entry surface 38 of the housing 30 and the type of analyte A. The osmosis coefficient is an inherent coefficient, which is dependent on the material, thickness, and structure (single layer or plural layers) of the entry surface 38 of the housing 30, for example.

If the osmosis coefficient δ is of a relatively large value, then since the value of the left side of equation (9), i.e., a change in the quantified value $[A_0(t)]$ per unit time, is large, the transition time required to reach a steady state, i.e., a state in which $[A(t)]=[A_0(t)]$, is short. Stated otherwise, even if the concentration [A(t)] changes sharply, the quantification following capability is high in a system in which the osmosis coefficient δ is of a relatively large value.

If the osmosis coefficient δ is of a relatively small value, then since a change in the quantified value $[A_0(t)]$ per unit time is small, the transition time required to reach a steady state is long. The effect of such a long transmission time on quantification accuracy will be described below.

Figure 20:
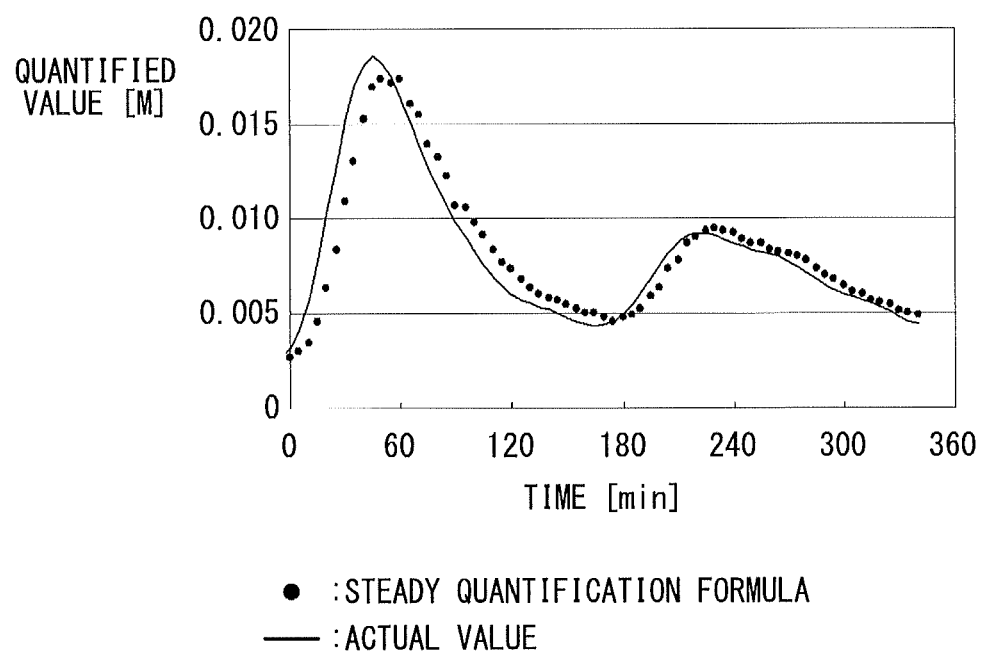
FIG. 20 is a graph showing quantified values of glucose, which are quantified according to a steady quantification rule.

FIG. 20 is a graph showing quantified values of glucose, which are quantified according to the steady quantification rule. The graph has a horizontal axis representing time (units: min) and a vertical axis representing load concentrations of glucose (units: M). In the graph, time-dependent changes in the concentration [A(t)] (actual values) of glucose are represented by the solid-line curve, whereas quantified values $[A_0(t)]$ acquired according to the steady quantification rule are plotted as solid dots. It is assumed that the entry surface 38 of the housing 30 (see FIG. 19) is coated with a protective film having a small osmosis coefficient (δ), for example.

As can be understood from FIG. 20, the quantified values are incapable of sufficiently following sharp changes in the actual values, and thus temporary gaps are developed between the quantified values and the actual values, resulting in substantial quantification errors. In particular, if the concentration [A(t)] is displayed on the display unit 28 (see FIG. 1) each time that the concentration [A(t)] is quantified, the reliability of the displayed value becomes problematic.

If the entry surface 38 of the housing 30 (see FIG. 19) is coated with a protective film having a sufficiently large osmosis coefficient (δ), the difference between the quantified value $[A_0(t)]$ acquired according to the steady quantification rule and the actual concentration [A(t)] is large, whereas the difference between the quantified value $[A_0(t)]$ acquired according to the non-steady quantification rule and the actual concentration [A(t)] is small.

According to the third embodiment, another concentration quantification rule is proposed, which is improved over the concentration quantification rule according to the first embodiment in view of the tendency of the above characteristics. A configuration and operations of a processor 90, which is capable of carrying out quantification calculations according to the improved concentration quantification rule, will be described below with reference to FIGS. 21 through 24.

Figure 21:
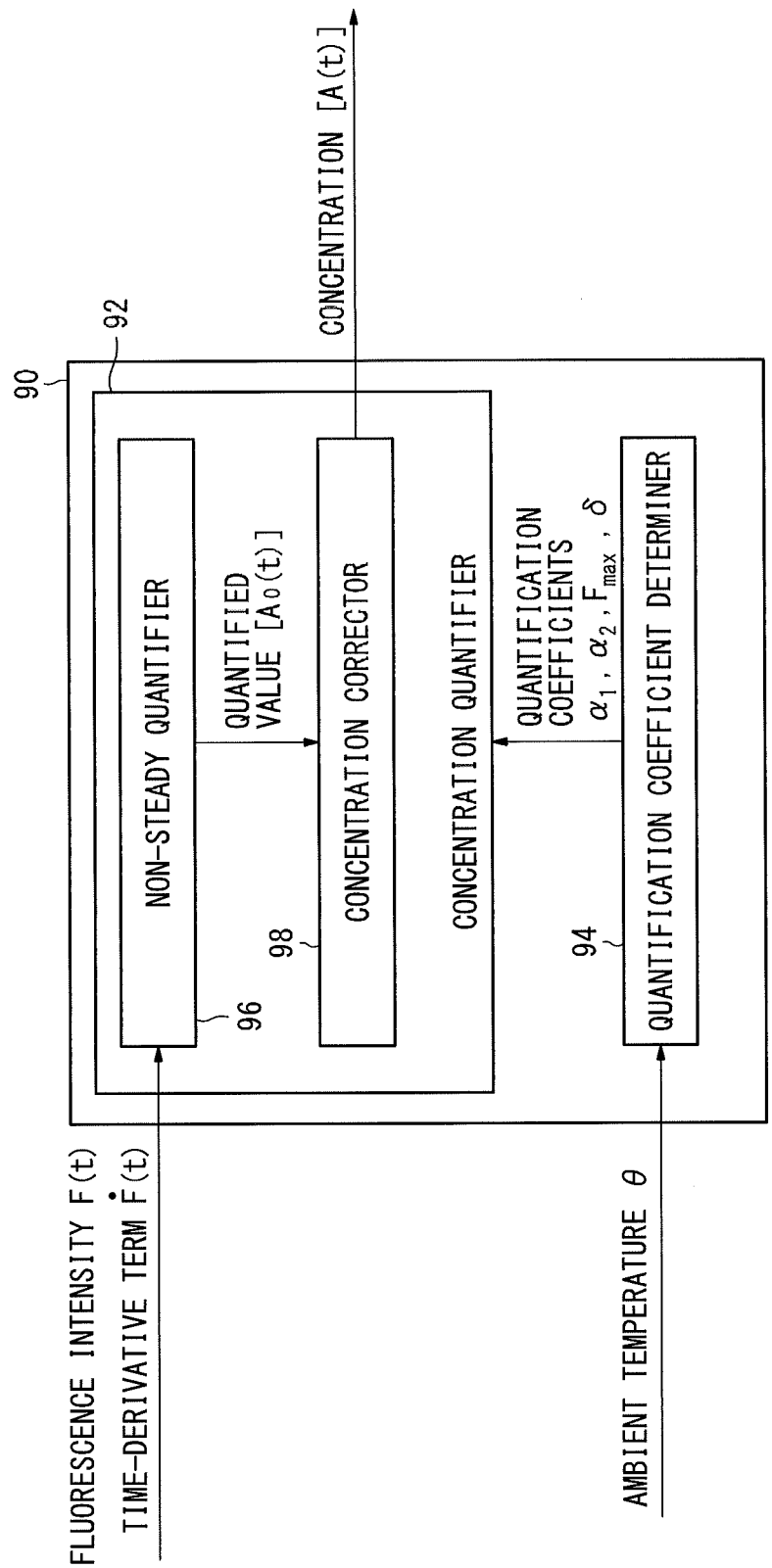
FIG. 21 is a functional block diagram of a processor according to the third embodiment.

As shown in FIG. 21, the processor 90 includes a concentration quantifier 92 for quantifying the concentration [A(t)] of analytes A in view of the degree of permeation, e.g., the permeation rate, through the fluorescence sensor 14, e.g., the housing 30, and a quantification coefficient determiner 94 for determining various quantification coefficients, e.g., $\alpha_1$, $\alpha_2$, $F_{max}$, δ, based on the ambient temperature θ acquired from the temperature sensor 15. The concentration quantifier 92 includes a non-steady quantifier 96 for calculating a quantified value $[A_0(t)]$ according to the non-steady quantification formula, and a concentration corrector 98 for correcting the quantified value $[A_0(t)]$ calculated by the non-steady quantifier 96 based on the degree of permeation, to thereby produce the concentration [A(t)].

Figure 22:
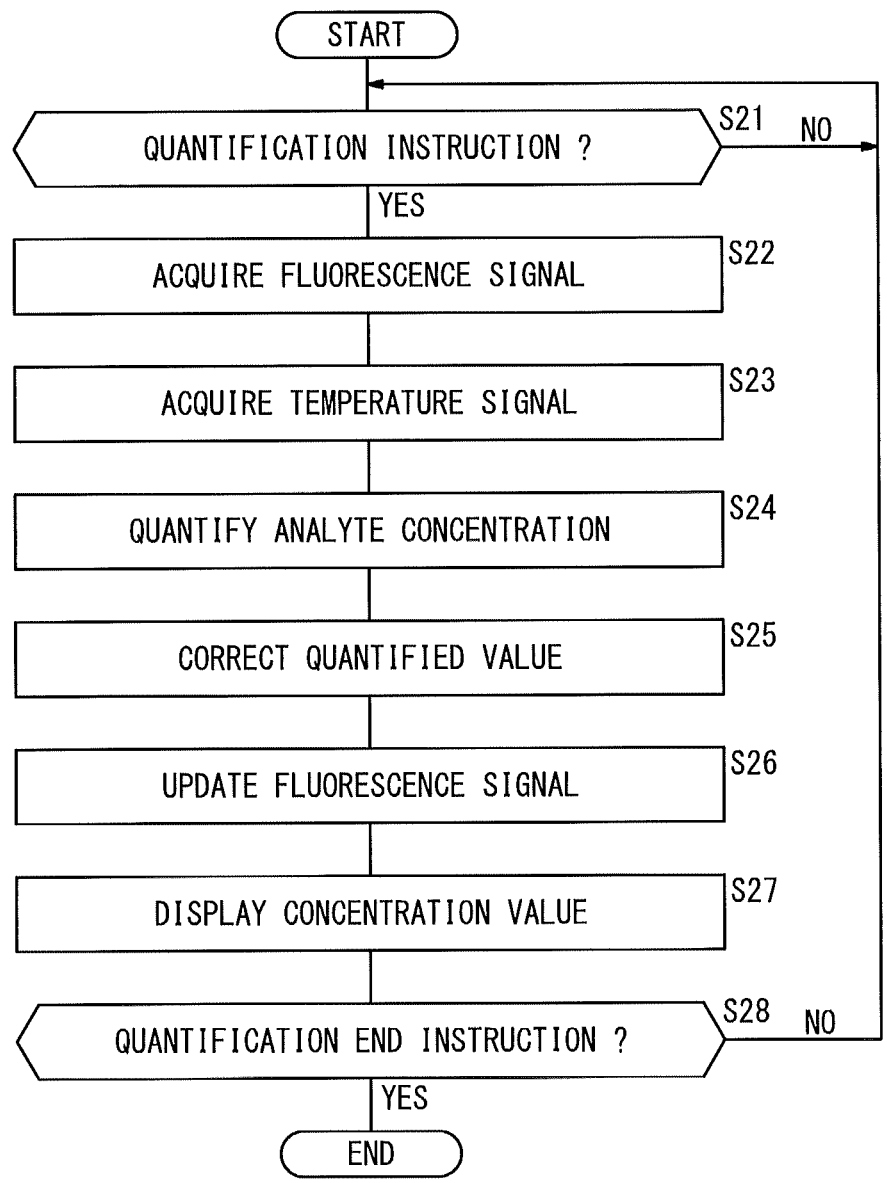
FIG. 22 is a flowchart of an operation sequence of the sensing device incorporating the processor shown in FIG. 21.

Operations of the sensing device 10, which incorporates the processor 90, will be described below with reference to the flowchart shown in FIG. 22. Operational details, which are identical to those according to the first embodiment (see FIG. 7), will not be described below.

Steps S21 through S23 and steps S26 through S28 are the same as steps S1 through S3 and steps S6 through S8 according to the first embodiment (see FIG. 7) and will not be described below.

In step S24, the non-steady quantifier 96 calculates a quantified value $[A_0(t)]$ according to a predetermined concentration quantification formula. More specifically, the non-steady quantifier 96 calculates a quantified value $[A_0(t)]$ according to the following equation (10):

$$[A_0(t)] = \frac{\dot{F}(t) + \alpha_2 F(t)}{\alpha_1 \{F_{max} - F(t)\}} \quad (10)$$

Equation (10) is basically the same as equation (4), and corresponds to the non-steady quantification formula with $\gamma=1$. However, equation (10) differs from equation (4) in that the quantification coefficient $\alpha_3$ in equation (4) is replaced with a different quantification coefficient ($\alpha_3 \rightarrow \alpha_1 \cdot F_{max}$), where $F_{max}$ represents a quantification coefficient in connection with the maximum value of the fluorescence intensity $F(t)$.

Prior to calculation of the quantified value $[A_0(t)]$, the quantification coefficient determiner 94 calculates quantification coefficients $\alpha_1, \alpha_2, F_{max}, \delta$. In view of the tendency for the optimum values of the quantification coefficients $\alpha_1, \alpha_2$ to change depending on the ambient temperature $\theta$, the quantification coefficient determiner 94 may sequentially update the values of the quantification coefficients $\alpha_1, \alpha_2$ based on the ambient temperature $\theta$ acquired from the temperature sensor 15.

Figure 23:
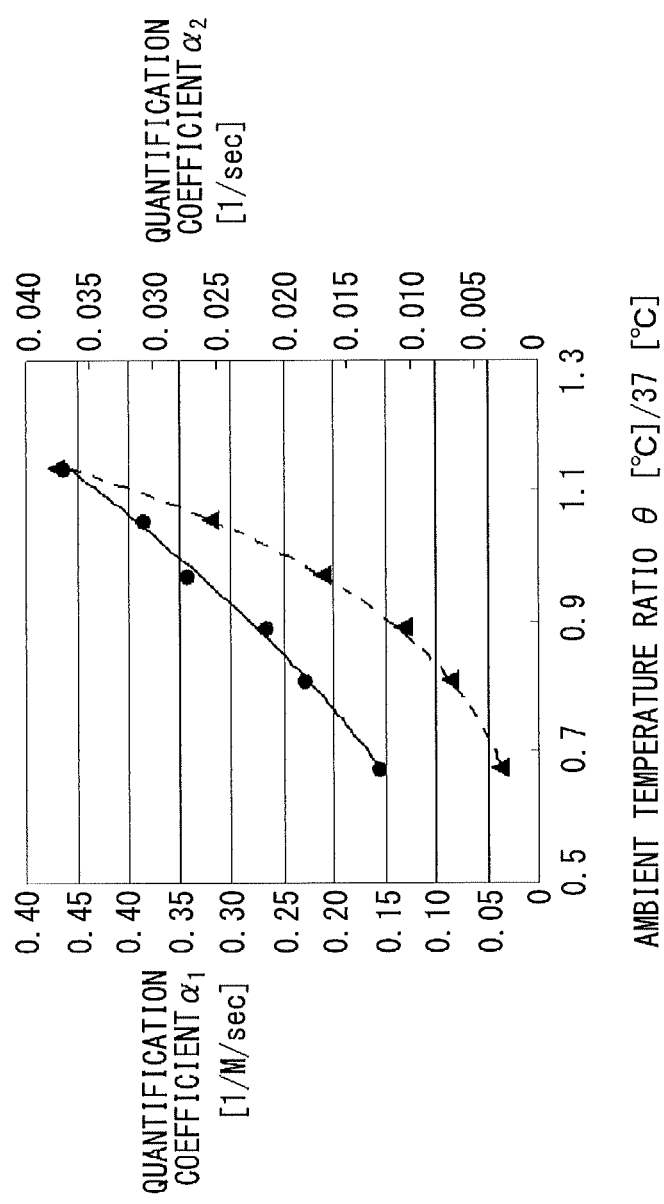
FIG. 23 is a graph showing an example of quantification coefficients according to the third embodiment.

FIG. 23 is a graph showing an example of determining the quantification coefficients $\alpha_1, \alpha_2$. The graph has a horizontal axis representing relative ratios of the ambient temperature $\{=\theta(°C.)/37(°C.)\}$, and a vertical axis representing the quantification coefficient $\alpha_1$ (indicated by the solid-line curve, units: $M^{-1}s^{-1}$) and the quantification coefficient $\alpha_2$ (indicated by the broken-line curve, units: $s^{-1}$). In FIG. 23, the quantification coefficients $\alpha_1, \alpha_2$ are determined by respective exponential functions, which are obtained by way of exponential approximation, based on plotted values suitable for six ambient temperatures $\theta$ in the vicinity of 37 (° C.).

In step S25, the concentration corrector 98 corrects the quantified value $[A_0(t)]$ that was calculated in step S24. The concentration corrector 98 calculates the quantified value $[A(t)]$ according to the following equation (11):

$$[A(t)]=[A_0(t)]+[\dot{A}_0(t)]/\delta \qquad (11)$$

Equation (11) corresponds to the results obtained by modifying equation (9) and solving for the concentration $[A(t)]$. The second term of the right side of equation (11) serves as a corrective term.

As described above, the processor 90 obtains the concentration $[A(t)]$ of analytes A as time-series data at quantification times t, in view of the degree of permeation of the analytes A into the fluorescence sensor 14. The quantification following capability achieved when the sensing method is carried out according to the third embodiment will be described below.

Figure 24:
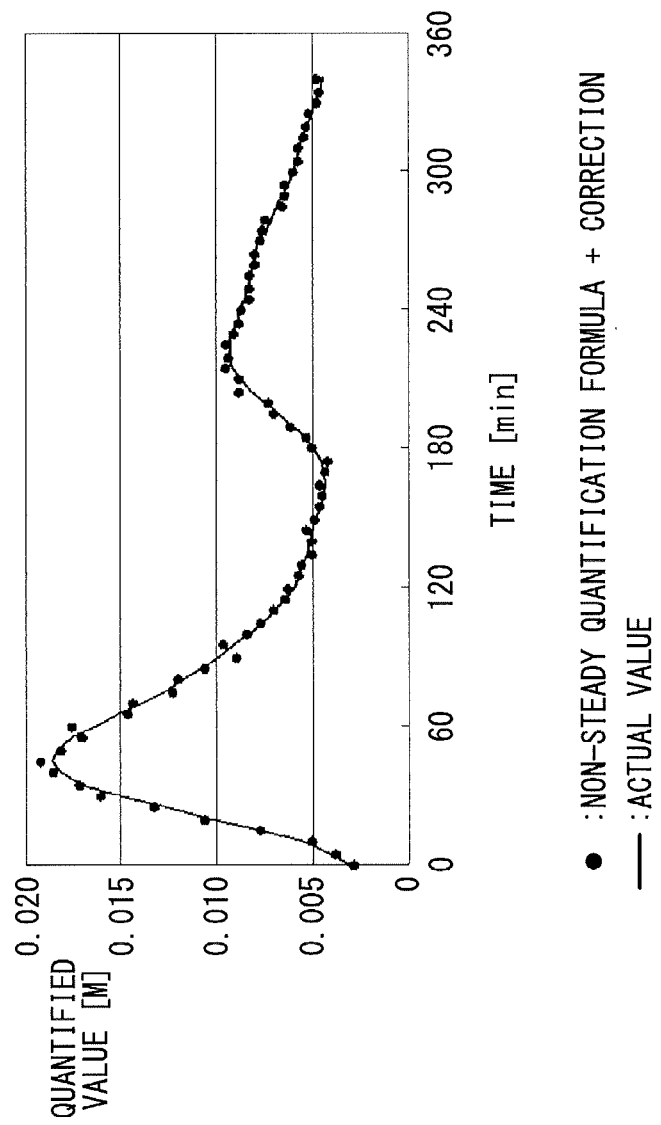
FIG. 24 is a graph showing quantified values of glucose, which are quantified according to a non-steady quantification rule and a correction process.

FIG. 24 is a graph showing quantified values of glucose, which are quantified according to a non-steady quantification rule, and a correction process. The graph has a horizontal axis representing time (units: min) and a vertical axis representing load concentrations of glucose (units: M). In the graph, time-dependent changes in the concentration $[A(t)]$ (actual values) of glucose are represented by the solid-line curve, whereas the concentration $[A(t)]$, which is acquired by quantification calculations according to the non-steady quantification rule and correction calculations, is plotted as solid dots. As can be seen from FIG. 24, the quantification following capability is confirmed to be much higher than with the quantified results (plotted values) shown in FIG. 20. In other words, a reduction in quantification accuracy due to a time delay in the reaction and permeation of analytes A can be prevented from occurring.

Correction of the quantified value $[A_0(t)]$ according to the non-steady quantification formula has been described above. Such a correction, which is carried out by means of the above method of the quantified value $[A_0(t)]$ acquired according to the steady quantification formula, also is effective to a certain extent. However, it has been confirmed by actual measurements that the non-steady quantification formula is more effective to produce noticeable advantages.

The present invention is not limited to the above embodiments, but changes and modifications can freely be made to the embodiments without departing from the scope of the invention. For example, the configurations shown in the first through third embodiments and modifications thereof may be implemented together in appropriate combinations.

The invention claimed is:

1. A sensing method of quantifying a concentration of analytes based on an intensity of fluorescence, which changes due to an interaction between the analytes and a labeled compound, comprising:
   an acquisition step of acquiring the intensity of fluorescence at a predetermined quantification time using a fluorescence sensor;
   a selection step of selecting a concentration quantification rule from a steady concentration quantification rule in relation to the intensity of fluorescence and a non-steady concentration quantification rule representative of a relationship between the acquired intensity of fluorescence and a time derivative of the intensity of fluorescence at the predetermined quantification time, depending on a time-dependent change in the acquired intensity of fluorescence and/or an ambient temperature; and
   a quantification step of quantifying the concentration of the analytes according to the selected concentration quantification rule.

2. The sensing method according to claim 1, wherein the non-steady concentration quantification rule is determined based on a chemical reaction formula representative of a bond dissociation reaction between the analytes and the labeled compound.

3. The sensing method according to claim 1, wherein the selection step selects the steady concentration quantification rule if the ambient temperature exceeds a first threshold value, and selects the non-steady concentration quantification rule if the ambient temperature does not exceed the first threshold value.

4. The sensing method according to claim 1, wherein the selection step selects the steady concentration quantification rule if the time-dependent change in the intensity of fluorescence does not exceed a second threshold value, and selects the non-steady concentration quantification rule if the time-dependent change in the intensity of fluorescence exceeds the second threshold value.

5. The sensing method according to claim 1, wherein the selection step further selects the concentration quantification rule from a plurality of non-steady concentration quantification rules having different degrees of contribution of the time derivative.

6. The sensing method according to claim 5, wherein the selection step increases the degrees of contribution as the ambient temperature decreases.

7. The sensing method according to claim 5, wherein the selection step increases the degrees of contribution as the time-dependent change in the intensity of fluorescence increases.

8. The sensing method according to claim 1, further comprising:
   a changing step of changing a sampling interval for the intensity of fluorescence depending on the time-dependent change in the intensity of fluorescence and/or the ambient temperature.

9. The sensing method according to claim 1, further comprising:
   a correction step of correcting the quantified concentration of the analytes depending on a degree of permeation of the analytes into the fluorescence sensor.

10. A sensing device for quantifying a concentration of analytes based on an intensity of fluorescence, which changes due to an interaction between the analytes and a labeled compound, comprising:
- a fluorescence sensor for acquiring the intensity of fluorescence at a predetermined quantification time;
- a quantification rule selector for selecting a concentration quantification rule from a steady concentration quantification rule in relation to the intensity of fluorescence and a non-steady concentration quantification rule representative of a relationship between the intensity of fluorescence acquired by the fluorescence sensor and a time derivative of the intensity of fluorescence at the predetermined quantification time, depending on a time-dependent change in the intensity of fluorescence acquired by the fluorescence sensor and/or an ambient temperature; and
- a concentration quantifier for quantifying the concentration of the analytes according to the concentration quantification rule selected by the quantification rule selector.

11. The sensing device according to claim 10, wherein the non-steady concentration quantification rule is determined based on a chemical reaction formula representative of a bond dissociation reaction between the analytes and the labeled compound.

12. The sensing device according to claim 10, wherein the quantification rule selector selects the steady concentration quantification rule if the ambient temperature exceeds a first threshold value, and selects the non-steady concentration quantification rule if the ambient temperature does not exceed the first threshold value.

13. The sensing device according to claim 10, wherein the quantification rule selector selects the steady concentration quantification rule if the time-dependent change in the intensity of fluorescence does not exceed a second threshold value, and selects the non-steady concentration quantification rule if the time-dependent change in the intensity of fluorescence exceeds the second threshold value.

14. The sensing device according to claim 10, wherein the quantification rule selector further selects the concentration quantification rule from a plurality of non-steady concentration quantification rules having different degrees of contribution of the time derivative.

15. The sensing device according to claim 14, wherein the quantification rule selector increases the degrees of contribution as the ambient temperature decreases.

16. The sensing device according to claim 14, wherein the quantification rule selector increases the degrees of contribution as the time-dependent change in the intensity of fluorescence increases.

17. The sensing device according to claim 10, further comprising;
- a sampling interval changer for changing a sampling interval for the intensity of fluorescence depending on the time-dependent change in the intensity of fluorescence and/or the ambient temperature.

18. The sensing device according to claim 10, wherein the concentration quantifier corrects the quantified concentration of the analytes depending on a degree of permeation of the analytes into the fluorescence sensor.

* * * * *